US007435538B2

(12) United States Patent
Endo et al.

(10) Patent No.: US 7,435,538 B2
(45) Date of Patent: Oct. 14, 2008

(54) HIGH THROUGHPUT SCREENING METHOD OF DRUG FOR PHYSIOLOGICALLY ACTIVE PROTEIN

(75) Inventors: Yaeta Endo, Matsuyama (JP); Tatsuya Sawasaki, Matsuyama (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 54 days.

(21) Appl. No.: 10/571,081

(22) PCT Filed: Sep. 8, 2004

(86) PCT No.: PCT/JP2004/013071

§ 371 (c)(1),
(2), (4) Date: Mar. 31, 2006

(87) PCT Pub. No.: WO2005/024428

PCT Pub. Date: Mar. 17, 2005

(65) Prior Publication Data

US 2006/0177813 A1 Aug. 10, 2006

(30) Foreign Application Priority Data

Sep. 8, 2003 (JP) ............................ 2003-316081

(51) Int. Cl.
*C12Q 1/70* (2006.01)
*C12Q 1/37* (2006.01)
*C12Q 1/18* (2006.01)

(52) U.S. Cl. ............................... 435/5; 435/23; 435/32

(58) Field of Classification Search ....................... None
See application file for complete search history.

(56) References Cited

U.S. PATENT DOCUMENTS

| | | | | |
|---|---|---|---|---|
| 2002/0094523 | A1* | 7/2002 | Sakalian et al. | 435/5 |
| 2003/0207290 | A1* | 11/2003 | Kenten et al. | 435/6 |
| 2005/0042305 | A1* | 2/2005 | Endo et al. | 424/725 |

FOREIGN PATENT DOCUMENTS

| | | | |
|---|---|---|---|
| JP | 2000-139468 A | | 5/2000 |
| JP | 2004-113186 A | | 4/2004 |
| WO | WO 03/064671 | * | 8/2003 |
| WO | WO 2003/064671 A1 | | 8/2003 |

OTHER PUBLICATIONS

Schleif et al. "In vitro translation systems from higher organisms." IN:Practical Methods in Molecular Biology, Springer-Verlag, New York. 1981. pp. 161-166.*
Heinz et al (Antimicrobial Agents and Chemotherapy 40:276-270, 1996).*
Anand et al (Science 300:1763-1767, Jun. 13, 2003, published online May 13, 2003).*
English translation of International Preliminary Report on Patentability and Written Opinion of the International Searching Authority for PCT/JP2004/013071 mailed Jul. 5, 2006.
Heinz et al., "Simple In Vitro Translation Assay to Analyze Inhibitors of Rhinovirus Proteases," Antimicrobial Agents and Chemotherapy, vol. 40, No. 1, Jan. 1996, pp. 267-270.
Anand et al., "Coronavirus Main Proteinase ($3CL^{pro}$) Structure: Basis for Design of Anti-SARS Drugs," Science, vol. 300, Jun. 13, 2003, pp. 1763-1767.
Marra et al., "The Gemome Sequence of the SARS-Associated Coronavirus," Science, vol. 300, May 30, 2003, pp. 1399-1404.
Copy of International Search Report for PCT/JP2004/013071 dated Dec. 7, 2004.
Copy of International Preliminary Report on Patentability for PCT/JP2004/013071 mailed Mar. 23, 2006.

* cited by examiner

*Primary Examiner*—Mary E Mosher
(74) *Attorney, Agent, or Firm*—Kilyk & Bowersox, P.L.L.C.

(57) ABSTRACT

The present invention is intended to provide a safe and quick means for screening a drug to a bioactive protein, in particular, an inhibitor, using a cell-free protein synthesis system with the use of a wheat embryo extract solution. The present inventors have strenuously studied to solve the matters above and finally completed the present invention by, in a system with the use of a wheat embryo, among cell-free protein synthesis means, constructing a synthesis system of a bioactive protein while sustaining its activities, and constructing a system for screening an inhibitor candidate to SARS $3CL^{pro}$, as an example using the synthesis system.

5 Claims, 6 Drawing Sheets

Determination of Activity of Full - length SARS Protease

1: GFP-GUS ( substrate ) alone
2: GFP-GUS
+ SARS protease (0.3 μl)
3: GFP-GUS
+ SARS protease (1.0 μl)

Determination of Activity of GST Fusion Protease by Autodigestion Reaction

A

B

Determination of Activity of GFP Fusion Protease by Autodigestion Reaction

Change in Fluorescence Intensity by Autodigestion Reaction

1: GFP-SARS pro (C145A)
2: GFP-SARS pro

① : only GFP-RS-GUS
② : +SA3CL (positive control)
③ : +SA3CL+Inhibitor candidateA
④ : +SA3CL+Inhibitor candidateB
⑤ : +SA3CL/C145A (negative control)

HIGH THROUGHPUT SCREENING METHOD OF DRUG FOR PHYSIOLOGICALLY ACTIVE PROTEIN

This application is a National Stage Application of PCT/JP2004/013071, filed Sep. 8, 2004.

TECHNICAL FIELD

The present invention relates to a safe and quick method for searching a drug to a bioactive protein, in particular, an inhibitor, using a cell-free protein synthesis system with the use of a wheat embryo extract. Specifically, a protein is synthesized in vitro safely, handy, and efficiently from a gene in a same reaction system, based on base sequence information in a pathogen including viruses, without being constrained by regulations for recombinant experiments from biohazard issues and others. Furthermore, the present invention relates to a method for screening a drug, in particular, an inhibitor, by using a cell-free protein synthesis system which can co-translationally trace the activity of a bioactive protein, wherein in a reaction system similar to an intracellular environment, the method uses the reactivities to the bioactive protein's autodigestion, recognition of a substrate, function, structure and others in a translation or folding process as an indicator.

BACKGROUND ART

As a method to conduct intracellular protein synthesis ex vivo, such as in a test tube, an in vitro cell-free protein synthesis method has been widely researched, wherein ribosome, for example, and other components necessary for protein synthesis are extracted from an organism (herein sometimes referred to as “wheat embryo extract for cell-free protein synthesis”) and used (Patent Documents 1, 2, 3, 4 and 5).

The cell-free protein synthesis system is a useful method, which keeps performance comparable to the system in a living cell concerning accuracy and speed of translation reaction, and can provide a target protein without carrying out a complicated purification step. Therefore, the more effective application of the synthesis system for industrial uses needs, in addition to increasing synthesis efficiencies, providing a wheat embryo extract-containing solution for use in synthesis and a ready-made type wheat embryo extract-containing solution steadily and at a retained high quality.

Meanwhile, the infection caused by a pathogen including viruses, even though it has been overcome to some extent by progress in chemotherapy and so on, is still a big threat to human, as can be seen from year-by-year epidemic of influenza, the occurrence of novel infectious diseases such as AIDS, *E. Coli* O157, SARS, West Nile virus, and Ebola hemorrhagic fever or from the reoccurrence of tuberculosis which was believed to have been overcome for a while. Under these circumstances, it has recently been demonstrated that a protease inhibitor to HIV virus is effective as an anti-AIDS drug, and it is put into practical use. The research for an infectious disease treatment medicament to target a protease which is indispensable for viral proliferation is believed to be more important in future.

At present, in a commonly conducted research on a protease inhibitor, an *E. Coli* or the like is treated by genetic recombination technology to produce a protease protein, which is then coexisted with the substrate protein and a test substance to search for an effective substance as an inhibitor using a substrate cleaving activity as an indicator. However, the production of a protein from a pathogen by genetic recombination needs a large scale experiment facility at a level of P3 and P4 is required and subjects itself to many regulatory constraints. In addition, a researcher can not perfectly be exempted from the risk to be infected with those pathogens even if protected by sufficient facilities.

Further, according to a conventional method, a drug, which is determined by an in vitro experiment to have a protease inhibitory activity, can in some cases not inhibit viral proliferation. It is suggested that the drug according to the conventional method is purified to complete its folding so that it may have a different structure to affect substrate-specificity.

In addition, recent infectious diseases of concern, SARS (severe acute respiratory syndrome) is an emerging infectious disease appeared in early 2003, and has affected 8,447 people and deprived 811 lives worldwide as of the end of June in 2003. SARS is characterized by high fever, malaise, ague, headache and dyspnoea, and progressed to cause interstitial pneumonia, requiring intubation and mechanical respiration. Currently, the fatality rate in the SARS infected is as high as approximately 15%, and it is believed that the infection route is mainly by direct contact although other routes cannot be fully excluded. From the many evidences, as a novel coronavirus exists in persons infected with SARS, the responsible pathogen for SARS is believed to be a novel coronavirus (SARS-CoV). Further, an essential proteinase for SARS-CoV's self-reproduction is found out, and it is pointed out that the catabolic enzyme shows important functions in the viral life cycle while causing SARS's symptoms (Nonpatent Document 2). Therefore, a proteinase for SARS-CoV (SARS $3CL^{pro}$) is considered to be a drug target effective in SARS treatment, and diverse researches have been conducted.

Until now, the following pharmacological researches on SARS have been proceeded by a number of groups. Study on candidate inhibitors of SARS $3CL^{pro}$ in molecular modeling for the three dimensional structural analysis of SARS $3CL^{pro}$'s crystalline structure, which is a primary proteinase for SARS-CoV (Nonpatent Document 1). Study on candidate drugs to SARS in molecular modeling for the binding mechanism between SARS $3CL^{pro}$ and ligands (Nonpatent Document 2). They have not experimentally examined SARS $3CL^{pro}$ and inhibitors thereto, and not reached to practical application.

Further, as the study of an inhibitor to the pathogen using a cell-free protein synthesis system, a method for screening an inhibitor to inhibit autodigestion is proposed wherein a rhinovirus protease is expressed in a cell-free protein synthesis system derived from rabbit's reticulocytes. However, that screening method is not practical because, for example, to screen enormous candidate drugs using a cell-free protein synthesis system derived from rabbit's reticulocytes needs a plenty of synthesis solution to obtain, has a problem in cost, and further requires a tracer experiment to execute using a radioisotope for the screening detection due to the slight amount of expressed protein in the synthesis system of interest (Nonpatent Document 3).

In spite of the above situation in SARS study, currently no effective drug for treating SARS has been available. The reasons are as follows: SARS-CoV has been recently identified to be the pathogen of SARS. Furthermore, to study such a highly-fatal virus as SARS pathogen, the experiment is difficult to manage because of constrains from biohazard. Moreover, it has been believed that a bioactive protein expressed from a decoded genomic sequence is difficult to screen while it keeps activity, because of problems from its conformation and posttranslational modification.

[Patent Document 1] Japanese Patent Application Laid-open No. Hei 6-98790

[Patent Document 2] Japanese Patent Application Laid-open Hei 6-225783

[Patent Document 3] Japanese Patent Application Laid-open Hei 7-194

[Patent Document 4] Japanese Patent Application Laid-open Hei 9-291

[Patent Document 5] Japanese Patent Application Laid-open Hei 7-147992

[Patent Document 6] International Patent Application PCT/US98/25742

[Nonpatent Document 1] Anand K, Ziebuhr J, Wadhwani P, Mesters J R, Hilgenfeld R.

Coronavirus main proteinase (3Clpro) structure:basis for design of anti-SARS drugs. Science. 2003 Jun. 13; 300 (5626):1763-7. Epub 2003 May 13.

[Nonpatent Document 2] Kuo-Chen Chou, Dong-Qing Wei, and Wei-Zhu Zhong.

Binding mechanism of coronavirus main proteinase with ligands and its implication to drug design against SARS. Biochemical and Biophysical Research Communications 308 (2003) 148-151

[Nonpatent Document 3] BEVERLY A. HEINZ, JOSEPH TANG, JEAN M. LABUS, FREDERICK W. CHADWELL, STEPHEN W. KARLDOR, AND MARLYS HAMMOND Simple In Vitro Translation Assay To Analyze Inhibitors of Rhinovirus Proteases ANTIMICROBIAL AGENTS AND CHEMOTHERAPY, January 1996, p. 267-270

DISCLOSURE OF THE INVENTION

An object of the present invention is to provide a safe and quick means for screening a drug to a bioactive protein, in particular, an inhibitor, using a cell-free protein synthesis system with the use of a wheat embryo extract. Another object of the present invention is to provide a non-conventional means for screening a drug to a bioactive protein, in particular, an inhibitor, using a cell-free protein synthesis system with the use of a wheat embryo extract which allows co-translational trace of the activity of the bioactive protein, wherein in a reaction system similar to an intracellular environment, the means uses the reactivities of the bioactive protein such as autodigestion, substrate recognition, function, structure and others in a translation or folding process as an indicator.

The present inventors have strenuously studied to solve the above problems and finally completed the present invention by constructing a synthesis system of a bioactive protein with its bioactivities kept in a cell-free protein synthesis means with the use of a wheat embryo, and constructing a system for screening an inhibitor candidate to SARS $3CL^{pro}$ as an example using the synthesis system.

Therefore, the present invention is composed of:

1. A method for searching a drug to a bioactive protein using a cell-free protein synthesis means with the use of a wheat embryo extract solution comprising at least steps 3) to 5) of the following steps:
   1) synthesizing a gene comprising a gene encoding the bioactive protein, wherein the step is based on base sequence information of the bioactive protein gene,
   2) synthesizing an mRNA from the gene synthesized in step 1),
   3) synthesizing the bioactive protein using a cell-free protein synthesis system with the use of a wheat embryo extract solution, using the mRNA synthesized in step 2) as a translation template or the gene synthesized in step 1) as a transcription template,
   4) determining the reactivity of a candidate drug to the bioactive protein by adding the candidate drug to the cell-free protein synthesis system with the use of a wheat embryo extract solution, and
   5) screening a drug to the bioactive protein by using the reactivity as an indicator.
2. The method for searching a drug according to the preceding 1, wherein the indicator of reactivity to the bioactive protein is based on the reactivity to bioactive protein's autodigestion.
3. The method for searching a drug according to the preceding 1, wherein the indicator of reactivity to the bioactive protein is based on the reactivity to the bioactive protein's substrate recognition.
4. The method for searching a drug according to the preceding 1, wherein the indicator of reactivity to the bioactive protein is based on the bioactive protein's autodigestion in a folding process, inhibition or termination of folding, or induction of misfolding.
5. The method for searching a drug according to the preceding 1, wherein the reactivity of the candidate drug to the bioactive protein is selected from any one, two or more of the following:
   1) a reaction of inhibiting or terminating a synthesis of the bioactive protein's mRNA in a transcription process,
   2) a reaction of inhibiting and/or antagonizing autodigestion at one, two or more autodigestion site(s) in the bioactive protein,
   3) a reaction of inhibiting and/or antagonizing the recognition of a substrate at one, two or more site(s) for recognizing a substrate in the bioactive protein,
   4) a reaction of inhibiting or terminating the synthesis of the bioactive protein in a translation process,
   5) a reaction of inhibiting or terminating the autodigestion or folding of the bioactive protein in a folding process, or a reaction of inducing misfolding,
6. The method for searching a drug according to any one of the preceding 1 to 5, wherein the steps 3) to 5) or 2) to 5) of the preceding 1 are conducted in a single reaction system.
7. The method for searching a drug according to any one of the preceding 1 to 6, wherein the wheat embryo extract solution is a cell-free protein synthesis means with a wheat embryo extract from which an endosperm and a low molecular synthesis inhibitor are substantially removed.
8. The method for searching a drug according to any one of the preceding 1 to 7, wherein the bioactive protein is a protein associated with pathogenic proliferation.
9. The method for searching a drug according to any one of the preceding 1 to 8, wherein the bioactive protein is a protease.
10. The method for searching a drug according to any one of the preceding 1 to 9, wherein the bioactive protein gene is a gene derived from any one of the following:
    1) a double-stranded DNA virus, 2) a singled-stranded DNA virus, 3) a positive-stranded RNA virus, 4) a negative-stranded RNA virus, 5) a double-stranded RNA virus, 6) a retrovirus, and 7) a hepadnavirus.
11. The method for searching a drug according to any one of the preceding 1 to 10, wherein the bioactive protein is any one of the following:

1) an RNA polymerase, 2) a DNA polymerase, 3) a helicase, 4) a coat protein, and 5) a capsid protein.

12. The method for searching a drug according to any one of the preceding 1 to 11, wherein the bioactive protein gene is derived from SARS.
13. A drug provided by the method for searching a drug according to any one of the preceding 1 to 12.
14. A reagent kit used in the method for searching a drug according to any one of the preceding 1 to 12.
15. An oligonucleotide primer to amplify a SARS $3CL^{pro}$ protein-encoding DNA.
16. The oligonucleotide primer according to the preceding 15, comprising any one of nucleotides represented by SEQ.ID.Nos: 6-21.
17. A SARS $3CL^{pro}$ protein-encoding DNA synthesized by using the oligonucleotide primer according to the preceding 15 or 16.
18. The SARS $3CL^{pro}$ protein-encoding DNA according to the preceding 17, represented by SEQ. ID. No:1.
19. A SARS $3CL^{pro}$ protein synthesized using a cell-free system with the use of a wheat embryo extract solution, using the DNA according to the preceding 17 or 18.
20. The SARS $3CL^{pro}$ protein according to the preceding 19, sustaining a protease activity.

The present invention has provided a safe and quick means for screening a drug to a bioactive protein, in particular, an inhibitor, using a cell-free protein synthesis system with the use of a wheat embryo extract. Furthermore, the present invention has succeeded in providing a means for screening a drug to a bioactive substance protein, in particular, an inhibitor, using the reactivities to bioactive protein's autodigestion, recognition of a substrate, or function, structure or others in a translation and/or folding process as an indicator.

DESCRIPTION OF THE PREFERRED EMBODIMENT (1) Preparation of Wheat Embryo Extract-containing Solution for Cell-Free Protein Synthesis A cell-free protein synthesis system used in the present invention uses a wheat embryo extract. Herein, the cell-free protein synthesis system means an in vitro synthesis method carried out by extracting components including, for example, ribosome, which is an intracellularly-equipped protein translation apparatus, from wheat embryo, and adding the transcription template or translation template, nucleic acids as the substrate, amino acids, energy source, various ions, buffer, and other useful factors to this extract solution. The system includes a system using RNA as template (hereinafter it is sometimes referred to as "cell-free translation system") and a system using DNA and reacting by the further addition of an enzyme necessary for transcription such as RNA polymerase (hereinafter it is sometimes referred to as "cell-free transcription/translation system"). The cell-free protein synthesis system in the present invention includes both of above described cell-free translation system and cell-free transcription/translated system.

A wheat embryo extract-containing solution used in the present invention is commercially available as PROTEIOS™ (from TOYOBO). As a preparation method of a wheat embryo extract solution, for the isolation method of wheat embryo, the method described in, for example, Johnston, F. B. et al., Nature, 179, 160-161 (1957) may be used, and for an extraction method from the isolated wheat embryo for a wheat embryo extract-containing solution, for example, the method described in Erickson, A. H. et al., (1996) Meth. In Enzymol., 96, 38-50 may be used. Besides them, the methods described in Japanese Patent Applications No. 2002-23139 and No. 2002-231340 may be mentioned.

A wheat embryo extract suitable for use in the present invention will be purified by removing almost all endosperm comprising components inhibiting protein synthesis function (components capable to influence the mRNA, tRNA, protein translation factors, ribosome and others, for example, tritin, thionine, ribonuclease and inhibit the function), which a material cell itself does contain or retain. Herein, the purified product from which almost all endosperm is removed means a wheat embryo extract remained after the removal of a endosperm portion to the extent that ribosome will not be substantially deadenylated, and further the extent that ribosome will not be substantially deadenylated means an extent that the ribosome has a deadenylation rate of less than 7% and preferably 1% or less.

The wheat embryo extract described above may comprise a protein derived from a wheat embryo extract-containing solution and a protein separately added according to need. In view of the preservation stability in a freeze-dried state, its usability and the like, the composition before freeze-dried has preferably a protein content of, but not limited in particular to, 1 to 10 weight % of the total composition, and more preferably 2.5 to 5 weight %, and further the lyophilized composition after freeze-dried has preferably a protein content of 10 to 90 weight % of the total lyophilized composition, and more preferably 25 to 70 weight %. Now, the protein content herein can be calculated by measuring its absorbance (260, 280 and 320 nm).

(2) Reduction of Deliquescent Substances in Solution Comprising Wheat Embryo Extract The wheat embryo extract-containing solution described above contains deliquescent substances such as potassium acetate and magnesium acetate from an extraction solvent or a buffer for use in gelfiltration after extraction. Thus, the wheat embryo extract-containing solution is used to prepare a translation reaction solution, which is then directly lyophilized to make a dry formulation with a trouble such as deliquescence, resulting in deterioration in quality of the formulation. The deterioration in quality means that the formulation is not completely dissolved in water, thereby to reduce synthesis activities in protein synthesis reaction. Therefore, the deliquescent substances in the wheat embryo extract-containing solution may be decreased in concentration to give no influence on the quality of the lyophilized formulation. The specific methods for decreasing deliquescent substances include, for example, a gel filtration method wherein a gel support is equilibrated beforehand with a deliquescent substance-reduced or free solution to use, or a dialysis method. By using these methods, the deliquescent substances in a solution finally prepared for translation reaction should be reduced to have a final concentration of 60 mM or less. Specifically, potassium acetate in the solution finally prepared for translation reaction should be reduced to have a concentration of 60 mM or less, and preferably 50 mM or less. Furthermore, the lyophilized formulation has preferably a deliquescent substance content of 0.01 parts by weight or less to 1 part by weight of the protein contained in the formulation, and particularly preferably 0.005 parts by weight or less to keep the preservation stability in the freeze-dried state.

(3) Elimination of Contaminant Microbes

As the wheat embryo extract-containing solution can be contaminated with spores of microbes, in particular a filamentous bacterium (mold) and the like, these microbes are preferred to be eliminated. Microbial proliferation may be seen in particular in a long-term (a day or higher) cell-free protein synthesis reaction, and hence is important to inhibit. The means of eliminating microbes preferably includes, but is not limited to, a filter for filter sterilization to use. The filter may not be limited in pore size to a particular one in so far as it can eliminate contamination-suspected microbes, but has usually a pore size of 0.1 to 1 μm, and preferably 0.2 to 0.5 μm.

(4) Method to Remove Low Molecular Synthesis Inhibitors from Wheat Embryo Extract-containing Solution In addition to the foregoing operations, a step for removing low molecular synthesis inhibitors can be added anywhere in the preparation of the wheat embryo extract-containing solution to make the solution suitable for cell-free protein synthesis of a bioactive protein with more preferable effects. A wheat embryo extract-containing solution prepared by substantially removing an endosperm component contains low molecular synthesis inhibitors having a protein synthesis inhibitory activity (this may be referred to as "low molecular synthesis inhibitor"). Thus, the removal of them may provide a wheat embryo extract-containing solution having a high protein synthesis activity. Specifically, the removal is conducted by fractionally removing low molecular synthesis inhibitors from the components of a wheat embryo extract-containing solution through the differences in their molecular weights. The low molecular synthesis inhibitor can be fractionally removed to have a smaller molecular weight than the least factor among those factors necessary for protein synthesis that are contained in the wheat embryo extract-containing solution. Specifically, the inhibitor may be fractionally removed to have a molecular weight of 50,000 to 14,000 or less, or preferably of less than 14,000. As the method for removing low molecular synthesis inhibitors from a wheat embryo extract-containing solution, a method already known per se, for example, dialysis using a dialysis membrane, gel-filtration, or ultrafiltration can be used. Among them, dialysis is preferred in view of, for example, the easiness of supplying an internal solution with materials.

As a dialysis membrane for use in the removing operation of low molecular synthesis inhibitors through dialysis, the one which can remove a molecule having a molecular weight of 50,000 to 12,000 may be mentioned, specifically, a recyclable cellulose membrane (from Viskase Sales, Chicago) which can remove a molecule having a molecular weight of 12,000 to 14,000, Spectra/Pore 6 (from SPECTRUM LABORATORIES INC., CA, USA) which can remove a molecule having the molecular weight of 50,000, and the like may preferably be used. A suitable amount of the wheat embryo extract-containing solution will be put toward the one-side of such dialysis membrane, and then dialysis be conducted by a conventional method. The dialysis is preferred to be conducted for 30 minutes to 24 hours.

While removing low molecular synthesis inhibitors, if an insoluble substance is produced in a wheat embryo extract-containing solution, inhibiting this production (hereinafter, this may be referred to as "the stabilization of a wheat embryo extract-containing solution") allows the wheat embryo extract-containing solution finally prepared or a solution for translation reaction to have a higher protein synthesis activity. As a specific method of stabilizing a wheat embryo extract-containing solution or a solution for translation reaction, there is mentioned a method wherein low molecular synthesis inhibitors described above are removed from a wheat embryo extract-containing solution or a solution for translation reaction with at least a high energy phosphate compound such as ATP or GTP (hereinafter, they may be referred to as "stabilization component") contained. As the high energy phosphate compound, ATP may preferably be used. Further, the removal may be preferably carried out from the solution with ATP and GTP, and more preferably ATP, GTP, and 20 kinds of amino acids contained.

The solution may be supplied with these stabilization components, incubated, and then subjected to the process for removing low molecular synthesis inhibitors. Alternatively, the stabilization component may be added also to an external solution for dialysis, and then the solution is subjected to dialysis to remove low molecular synthesis inhibitor. Advantageously, the stabilization component in the external solution for dialysis, even if decomposed during dialysis, can be constantly supplemented with the fresh stabilization component. This approach can be applied to gelfiltration and ultrafiltration used to give the same effect. The supports they use are equilibrated with a filtration buffer with a stabilization component contained, supplied with a wheat embryo extract-containing solution or a solution for translation reaction with a stabilization component contained, and the supplied with the above-described buffer to filtrate.

The amount of a stabilization component to add and the time of stabilization to treat may be selected as appropriate depending on the kind of a wheat embryo extract-containing solution and the method of preparation. As the selection method, there may be mentioned a method wherein a wheat embryo extract-containing solution is supplied with various stabilization components in amount and kind on a trial basis, and subjected to the step for removing low molecular synthesis inhibitors after an appropriate hour to give a treated wheat embryo extract-containing solution, which is then centrifuged to separate into the soluble compartment and the insoluble component, thereby to select a case resulting in a less amount of the insoluble component. Alternatively, a method is preferred wherein the treated wheat embryo extract-containing solution is used to carry out cell-free protein synthesis, thereby to select a case resulting in a high protein synthesis activity. Further, a method is mentioned wherein stabilization component is added in an external solution for dialysis, and then wheat embryo extract-containing solution is subjected to dialysis for an appropriate time, thereby to select based of the amount of the insoluble component in the solution thus obtained or the protein synthesis activity of the solution thus obtained.

As one example of the stabilizing condition of a wheat embryo extract-containing solution thus selected, specifically, if dialysis is carried out for the step of removing low molecular synthesis inhibitors, there is mentioned a method wherein the wheat embryo extract-containing solution and the external solution for dialysis are supplied with 100 μM to 0.5 mM of ATP, 25 μM to 1 mM of GTP and 25 μM to 5 mM of each 20 kinds of amino acids and then subjected to dialysis for 30 minutes to an hour or more. The temperature for dialysis may be any temperature so far as it does not deteriorate the protein synthesis activity of the wheat embryo extract-containing solution and allows dialysis. Specifically, the lowest temperature is a temperature at which the solution will not freeze, usually −10° C., and preferably −5° C. The highest temperature is a limit temperature which gives no bad influence on the solution used in dialysis, 40° C., and preferably 38° C.

In addition, if low molecular synthesis inhibitors are removed after a wheat embryo extract-containing solution is prepared, the solution needs no further the above stabilization component to add.

(5) Method for Decreasing Concentration of Reducing Agent in Wheat Embryo Extract-containing Solution The wheat embryo extract-containing solution, which contains a reducing agent at a decreased concentration, is used to execute cell-free protein synthesis, allowing production of a target bioactive protein which has an intramolecularly formed disulfide bond. For a method for decreasing a reducing agent in a wheat embryo extract-containing solution, there is used a method wherein a step of decreasing a reducing agent is employed anywhere in the steps for the preparation of the wheat embryo extract-containing solution. The reducing agent should be decreased to have so a concentration in the finally prepared wheat embryo extract-containing solution that the solution may be used to execute translation reaction, allowing synthesis of a bioactive protein which has an intramolecularly formed disulfide bond to sustain. Dithiothreitol (hereinafter, this may be referred to as "DTT") as a reducing agent is decreased to have a final concentration of 20 to 70 μM, and preferably 30 to 50 μM in the final solution for translation reaction prepared from a wheat embryo extract-containing solution. 2-mercaptoethanol is decreased to have a final concentration of 0.1 to 0.2 mM in the final solution for translation reaction. Glutathione/oxidized glutathione is decreased to have a final concentration of 30 to 50 μM/1 to 5 μM in the final solution for translation reaction. The specific concentration of a reducing agent is not limited to those described above and varies appropriately depending on the protein to synthesize or the kind of a cell-free protein synthesis system to use.

The method of selecting the optimal concentration range of a reducing agent is not limited in particular, and, for example, there is mentioned a selection method based on the effect of a catalyst for disulfide bond exchange reaction. Specifically, solutions for translation reaction are prepared from a wheat embryo extract-containing solution at various concentrations of a reducing agent, and then supplied with a enzyme capable of catalyzing disulfide bond exchange reaction to synthesize a bioactive protein having an intramolecular disulfide bond. In addition, as a control experiment, the same protein synthesis is carried out using the same solutions for translation reaction supplied with no enzyme capable of catalyzing disulfide bond exchange reaction. Then, the soluble component of a bioactive protein to synthesize is separated by a method such as centrifugation. The reaction solution, wherein this soluble component has a share of 50% (solubilization 50%) or more in the total and further has been increased by the addition of an enzyme capable of catalyzing disulfide bond exchange reaction, can be determined to be a suitable reaction solution for synthesizing a bioactive protein with an intramolecular disulfide bond retained. Furthermore, within the concentration range of a reducing agent selected based on the effect of the catalyst for disulfide bond exchange reaction as above described, the concentration of the reducing agent which can synthesize the highest amount of the bioactive protein can be selected as more preferable concentration range.

For specific methods for decreasing a reducing agent, there is used a method wherein a wheat embryo extract-containing solution is prepared to be free from a reducing agent, and then supplied with a reducing agent to have an above described concentration range together with necessary components for a cell-free protein synthesis system, or a method wherein a reducing agent is removed from a solution for translation reaction derived from a wheat embryo extract-containing solution to be within the concentration range described above. As a wheat embryo extract-containing solution for cell-free protein synthesis requires a high degree of reduction condition to extract, a method wherein a reducing agent is removed from the solution after extraction is easier to execute. As a method for removing reducing agent from a wheat embryo extract-containing solution, there is mentioned a method using a gelfiltration support. Specifically, for example, there is mentioned a method wherein Sephadex G-25 column is beforehand equilibrated with an appropriate buffer containing no reducing agent, and then fed with a wheat embryo extract-containing solution to pass through.

(6) Preparation of Solution for Translation Reaction

The wheat embryo extract-containing solution prepared as described above is supplied with a nuclease inhibitor, various ions, a substrate, an energy source and the like necessary for protein synthesis (hereinafter, they may be referred to as "additives for a solution for translation reaction") and an mRNA encoding a target bioactive protein, which acts as a translation template, and, if desired, a stabilizer which comprising a component selected from the group consisting of inositol, trehalose, mannitol, and sucrose-epichlorohydrin copolymer to prepare a solution for translation reaction. The concentrations of components to add may be provided from a compounding ratio well known per se.

The additives for a solution for translation reaction, specifically, include amino acids acting as substrate, an energy source, various ions, a buffer, an ATP-regenerating system, a nuclease inhibitor, a tRNA, a reducing agent, polyethylene glycol, a 3',5'-cAMP, a folate, an antimicrobial, and the like. Further, concerning each concentration, preferably, ATP is contained at 100 μM to 0.5 mM, GTP at 25 μM to 1 mM and 20 kinds of amino acids at their respective 25 μM to 5 mM. They can be selected and combined for use as appropriate according to the translation reaction system. Specifically, a wheat embryo extract, which is used for a wheat embryo extract-containing solution, is supplied with 20 mM of HEPES-KOH (pH 7.6), 100 mM of potassium acetate, 2.65 mM of magnesium acetate, 0.380 mM of spermidine (from Nacalai Tesque), respectively 0.3 mM of 20 kinds of L-amino acids, 4 mM of dithiothreitoll, 1.2 mM of ATP (from Wako Pure Chemical Industries, Ltd.), 0.25 mM of GTP (from Wako Pure Chemical Industries, Ltd.), 16 mM of phosphocreatine (from Wako Pure Chemical Industries, Ltd.), 1000 U/ml of Rnase inhibiter (from TAKARA) and 400 μg/ml of creatine kinase (from Roche), to dissolve sufficiently, followed by adding the mRNA translation template supporting an mRNA encoding a target bioactive protein.

Herein, the mRNA encoding the target bioactive protein has a structure wherein the sequence encoding a bioactive protein capable of being synthesized in a cell-free protein synthesis system consisting of wheat embryo is linked in the downstream of both an appropriate sequence recognized by RNA polymerase and further a sequence having a function to activate translation. The sequence recognized by RNA polymerase includes T3 or T7 RNA polymerase promoter. Further, in a cell-free protein synthesis system, as a sequence enhancing a translation activity, there may be preferably used a sequence having a structure wherein Ω sequence, Sp6 or the other is linked to the 5'-upstream of the coding sequence.

(7) Bioactive Protein

The bioactive protein according to the present invention is a protein synthesized based on the base sequence of an organism's gene and having specific functions derived from an organism. Further, the base sequence for a bioactive protein is not necessarily identical to the base sequence of an organism, but may be a base sequence into which modifications such as deletion, substitution, addition, insertion are appropriately introduced as long as the protein has specific functions. For example, a protein synthesized on the basis of the base sequence of the gene of a pathogen including viruses and having specific functions derived from the pathogen may be mentioned. As kinds of pathogens including viruses, double-stranded DNA viruses, singled-stranded DNA viruses, positive-stranded RNA viruses, negative-stranded RNA viruses, double-stranded RNA viruses, retroviruses, hepadnaviruses and the like may be mentioned but not limited in particular. Further, the bioactive protein of a specific function includes proteins associated with pathogenic proliferation, in more detail, a protease, a helicase, an RNA polymerase and the like, and also a coat protein and a capsid protein which are involved in the structural formation of viruses, but is not limited in particular.

In the present invention, the transcription/translation of a bioactive protein in a cell-free synthesis system with the use of a wheat embryo extract allows easier synthesis of a bioactive protein which sustains the tertiary structure in a almost native state and its activities, and further the simultaneous addition of a candidate drug in the synthesis system with the reaction allows easier screening for a useful candidate drug which targets autodigestion, recognition of a substrate, and the reaction in translating or folding process.

In the Examples, bioactive proteins were synthesized based on the amino acid sequence (GenBank's accession number AY274119) of the major proteinase of SARS-CoV which has previously disclosed, SARS $3CL^{pro}$. Therefore, on the basis of amino acid sequence the codons of each amino acid were examined and a primer was designed by selecting GC-rich codons so that the annealing site of the primer became shorter. The whole gene was synthesized using this primer through Inverse PCR. The SARS $3CL^{pro}$ was synthesized by obtaining mRNA from this gene and translating the mRNA as template in cell-free synthesis with the use of a wheat embryo extract. Then, based on the fact that the resulting SARS $3CL^{pro}$ sustained a protease activity, a drug screening system employing SARS $3CL^{pro}$ was constructed. However, this is disclosed just by way of a preferable illustration and not by way of limitation. The amino acids sequence of SARS $3CL^{pro}$ shown in Examples was presented in SEQ. ID. NO: 32.

(8) Method of Synthesizing Protein Using Cell Extract Solution for Cell-Free Protein Synthesis The wheat embryo extract solution, that is, a cell extract solution prepared as above for cell-free protein synthesis can be dissolved in a dissolving solution which is supplied with a deliquescent substance and water to have a concentration appropriate for protein synthesis reaction, and put into a selected system or apparatus already known per se to take place protein synthesis. As a system or apparatus for protein synthesis, there are mentioned a method such as the batch method (Pratt, J. M. et al., Transcription and Tranlation, Hames, 179-209; B. D. & Higgins, S. J., eds, IRL Press, Oxford (1984)) wherein a translation reaction solution in which the cell extract solution for cell-free protein synthesis of the present invention is dissolved is kept at an appropriate temperature for the synthesis, a cell-free protein synthesis system in a continuous manner (Spirin, A. S. et al., Science, 242, 1162-1164 (1988)) wherein amino acids, an energy source and others necessary for a cell-free protein synthesis system are fed into the reaction system continually, a dialysis method (Kigawa et al., The 21st The Molecular Biology Society of Japan, WID6), and a method wherein a solution containing amino acids, an energy source and others necessary for a cell-free protein synthesis system is overlaid onto a solution for translation reaction (bilayer system: Sawasaki, T., et al., 514, 102-105 (2002)).

Herein, when the cell extract for cell-free protein synthesis is used at a decreased concentration of a reducing agent, a solution for supplying amino acids, an energy source and others necessary for a cell-free protein synthesis system also is adjusted to have the same concentration of the reducing agent. Furthermore, the translation reaction is conducted in the presence of an enzyme capable of catalyzing disulfide bond exchange reaction to allow high efficient synthesis of a bioactive protein which retains an intramolecular disulfide bond. As the enzyme capable of catalyzing disulfide bond exchange reaction, for example, a protein disulphide isomerase may be mentioned. The amount of these enzymes to add to a cell-free translation system described above may be selected as appropriate depending on the kind of enzyme. Specifically, the solution for translation reaction, that is, a wheat embryo extract-containing solution which is extracted from wheat embryo and contains DTT as a reducing agent at 20 to 70 μM and preferably 30 to 50 μM is supplied with a protein disulfide isomerase to have a final concentration of 0.01 and 10 μM, and preferably 0.5 μM in the reaction solution for translation. Further, the addition is preferable in timing before the initiation of translation reaction in view of the efficiency of the formation of a disulfide bond.

(9) Screening Method

A screening method in a cell-free system with the use of a wheat embryo extract solution according to the present invention is a non-conventional method for screening a candidate drug comprising at least steps 3) to 5) of steps 1) to 5) as shown below. The conventional method for screening a candidate drug has been a method which mainly aims at, for example, the activities or structure of a matured protein. A cell-free protein synthesis system with the use of a wheat embryo extract solution of the present invention permits screening a drug to a bioactive protein in a state such as <1>, and <3> through <5> described below. Furthermore, combination of different indicators allows screening drugs which are different in mechanism of pharmacological effects and drugs having integral effects, as well as drugs which are appropriate for cocktail therapy against pathogens.

A method for searching a drug to a bioactive protein using a cell-free protein synthesis means with the use of a wheat embryo extract solution according to the present invention comprises the following steps 1) to 5):

1) Synthesizing a gene comprising a gene encoding the bioactive protein, wherein the step is based on base sequence information of the bioactive protein gene.

A labeling base sequence such as GFP, GUS and GST, and further the recognition sequence for the bioactive protein may also be added to the bioactive protein gene to provide the base sequence of the bioactive protein gene.

2) Synthesizing an mRNA from the gene synthesized in step 1).

The transcription process can be a previously known art.

3) Synthesizing the bioactive protein using the cell-free protein synthesis system with the use of a wheat embryo extract solution, using the mRNA synthesized in step 2) as a translation template or the gene synthesized in step 1) as a transcription template.

The cell extract-containing solution for cell-free protein synthesis is added by, for example, Pipetman and/or the channel pipette of an automatic pipetting device respectively to different wells of a container divided into a plurality of regions in an amount appropriate to the well. Subsequently, a solution comprising substances necessary for protein synthesis, the translation template or the transcription template, and a stabilizer are added to each well by, for example, Pipetman and/or the channel pipette of an automatic pipetting device in an amount of requirement to synthesize the bioactive protein.

4) Determining the reactivity of a candidate drug to the bioactive protein or bioactive protein's mRNA by adding the candidate drug to the cell-free protein synthesis system.

The candidate drug may be added at any time point in the bioactive protein synthesis system, during which a transcription step, a translation step, an autodigestion process, a substrate recognition step, and a folding step should occur. A drug can be added simultaneously with the translation step, to allow screening by targeting the folding step of the bioactive protein or the change in folding, which is a non-conventional screening means using a novel system.

5) Screening a drug to the bioactive protein by using the reactivity of a candidate drug to the bioactive protein as an indicator.

The method for determining the reactivity of a candidate drug to the bioactive protein qualitatively or quantitatively includes any method which may be served as long as it can detect the reactivity, and is not limited in particular. Specifically, a bioactive protein's site for recognizing a substrate or a bioactive protein to synthesize in a cell-free protein synthesis system may be labeled with a label to trace the reactivity to the bioactive protein qualitatively and quantitatively by using the label as a marker. As the labeling means in this instance, common means using such as deuterium, radioisotope, fluorescent substances, and color source substances may be mentioned. Further, a candidate drug, which can use the reactivity to the translation template for the bioactive protein as an indicator, can be judged qualitatively and quantitatively for the reactivity to the mRNA for the bioactive protein from the amount of expression of the bioactive protein synthesized in the cell-free protein synthesis system or the presence or absence of the expression of the labeled specific protein.

Further, a cell-free protein synthesis manner with the use of a wheat embryo extract liquid according to the present invention allows synthesis of a bioactive protein with bioactivity sustained. Therefore, the synthesized bioactive protein allows screening a candidate drug without the protein subjected to a purification step, and thus steps 3) through 5) or 2) through 5) indicated above can be conducted in a single reaction system.

Now below, the detection (determination) method of the present invention for using reactivity of a candidate drug to a bioactive protein as an indicator will be explained, and they are offered by way of illustration and not by way of limitation.

<1> Translation Reaction of mRNA for Bioactive Protein

In the translation process of the mRNA for a bioactive protein, the amount of the bioactive protein synthesized is detected by the addition of the candidate drug. The insertion of a marker sequence into the base sequence for a bioactive protein may provide the detection by the amount of the marker detected. Further, using SDS-PAGE, the presence or absence of the band of the bioactive protein, which is synthesized depending on the presence or absence of the candidate drug will be detected.

<2> Matured Bioactive Protein

Protease: A labeled substance comprising a protease cleavage recognition site is contacted with protease and a candidate drug, and then the labeled product is detected, or subjected to SDS-PAGE to detect the presence or absence and the position of the band for a peptide generated by protease cleavage.

RNA polymerase: a radiolabeled or fluorescence-labeled ribonucleotide and a candidate drug are reacted using DNA or RNA as template to detect no fresh RNA synthesized, wherein the product is separated by PAGE or capillary, and then detected by autoradiogram if a radiolabel is used, or excited by a laser or a mercury lamp to detect by wavelength through a polarized light filter if fluorescence used.

DNA polymerase: a DNA or RNA primer, radiolabeled or fluorescence-labeled deoxyribonucleotide, and a candidate drug are reacted using the DNA or the RNA as a template to detect no fresh DNA synthesized, wherein the product is separated by PAGE or capillary, and then detected by autoradiogram if a radiolabel is used, or excited by a laser or a mercury lamp to detect by wavelength through a polarized light filter if fluorescence used.

Helicase: a single-strand specific nuclease and a candidate drug are reacted using a radiolabel or fluorescence-labeled double-stranded DNA or RNA as a template to detect whether the template becomes shorter or not, wherein the product is separated by PAGE or capillary, and then detected by autoradiogram if a radiolabel is used, or excited by a laser or a mercury lamp to detect by wavelength through a polarized light filter if fluorescence used.

<3> Autodigestion Reaction of Bioactive Protein

A labeled substance comprising the autocleavage recognition site of a bioactive protein is contacted with the bioactive protein and a candidate drug, and then the labeled product is detected, or subjected to SDS-PAGE to detect the presence or absence and the position of the band for a peptide generated by protease cleavage. Alternately, a protein is synthesized to comprise an autocleavage recognition site sequence in the linker between the labeled substance and the bioactive protein, and the labeled product is detected.

<4> Bioactive Protein's Substrate Recognition Reaction

A substance comprising a substrate recognition sequence with a labeling substance contained, a bioactive protein and a candidate drug are contacted to detect change in fluorescence intensity, or subjected to SDS-PAGE to detect the contrast (including the presence or absence of the band) and the position of the band of the bioactive protein which has recognized the substrate.

<5> Folding Reaction of Bioactive Protein

It is detected from change in the tertiary structure using, for example, NMR and CD that a labeled bioactive protein and a candidate drug are reacted to terminate folding or to induce misfolding. Alternatively, it can be detected by reactivity with a monoclonal or a single chain antibody.

In order to screen an inhibitor candidate to SARS protease activity, a cell-free protein synthesis means with the use of a wheat embryo extract solution of the present invention is used to synthesize the SARS protease ($SA3CL^{pro}$) in a state for sustaining protease activity. Then, a substance (GFP-RS-GUS) containing cleavage site sequence RS with a labeling substance GFP contained, $SA3CL^{pro}$ and an inhibitor candidate are contacted to detect change in GFP fluorescence intensity, or subjected to SDS-PAGE to detect the presence or absence and the position of the band of GFP-RS-GU or GFP. Thereby, an inhibitor can be searched by using the decrease in GFP fluorescence intensity because of the inhibition of the RS cleavage in GFP-RS-GUS, or the change in contrast or the change in position of a GFP-RS-GU or GFP band (including the presence or absence of the band) as an indicator.

For a candidate drug according to the present invention, various kinds of compound libraries well known per se can be selected. The cell-free protein synthesis system with the use of a wheat embryo extract solution, which is not a screening system of living cell system using *E. Coli* and the like, can be used not only for a candidate drug affecting cell proliferation and a candidate drug hardly incorporated into a cell, but also for a candidate drug poorly soluble in water because the system can synthesize a protein in the presence of an organic solvent. Specifically, low molecular compound libraries, which are commercially available, may be mentioned.

Further, a reagent kit used in a method for searching a drug to a bioactive protein using a cell-free protein synthesis means with the use of a wheat embryo extract solution according to the present invention comprises at least a cell extract solution for cell-free protein synthesis. Furthermore, the reagent is used to synthesize a bioactive protein in a container divided into a plurality of regions, allowing high-throughput screening a candidate drug.

The present invention will be explained in details below with following examples, and the scope of the present invention will not be limited by these examples.

EXAMPLE 1

Detection of SARS 3CL Protease Activity (1) Cloning of Genetic DNA of SARS 3CL Protease A synthesized DNA, which had been designed from the information of amino acid sequence of a SARS 3CL protease gene, was used as a primer and pBSIIKS+ was used as a template to conduct Inverse PCR, thereby to fabricate SARS 3CL protease gene. Namely, the sense primer S1 (SEQ. ID. No:6) and the antisense primer A1 (SEQ. ID. No:14) were used to position in the both sides of HindIII site of pBSIIKS+, to conduct Inverse PCR, followed by treating with exonuclease I to remove unreacted primers. The obtained PCR product as template, S1 primer, S2 primer (SEQ. ID. No:7) which overlapped each other with A1 primer's end by respective 15 mers, and A2 primer (SEQ. ID. No:15) were used to conduct Inverse PCR. The obtained PCR product as template, S2 primer, S3 primer (SEQ. ID. No:8) which overlapped each other with A2 primer by respective by 15 mers, and A3 primer (SEQ. ID. No:16) were used to conduct Inverse PCR, thereby to amplify DNA. Subsequently, S3, A3, S4 (SEQ. ID. No:9), A4 (SEQ. ID. No:17), S5 (SEQ. ID. No:10), A5 (SEQ. ID. No:18), S6 (SEQ. ID. No:11), A6 (SEQ. ID. No:19), S7 (SEQ. ID. No:12), A7 (SEQ. ID. No:20), S8 (SEQ. ID. No:13) and A8 (SEQ. ID. No:21), which were designed to overlap by 15 mers in the same manner, were used to repeat Inverse PCR, thereby to amplify DNA. This plasmid was extracted with phenol/chloroform, cleaved with a restriction enzyme, HindIII (from NEB) and purified with GENE CLEAN II Kit (from Funakoshi Co., Ltd.). This purified restriction enzyme fragment was circularized by self-ligation. This circularized plasmid was transformed, plated onto the LB medium containing ampicillin (100 ppm) and cultivated overnight at 37° C. The colony of DNA having the aimed fragment length was selected from the colonies obtained by PCR, and finally the sequence was confirmed by sequencing. The colony having the aimed DNA fragments was downsized and this plasmid was amplified in *E. Coli*. Thereafter, to obtain the plasmid alone, it was purified using GenElute™ Plasmid Miniprep Kit (from SIGMA). The obtained vector (pBS-SA3CL$^{pro}$) was cleaved with restriction enzymes, Xho1 and BamH1 (from NEB), and pEU-E01-MCS vector was also cleaved with Xho1 and BamH1, purified with GENE CLEAN II Kit (from Funakoshi Co., Ltd), and then ligated in the same manner to obtain the plasmid {pEU-E01-SA3CL$^{pro}$ (SEQ. ID. No:1)}. This plasmid was subjected to PCR using SPu primer (SEQ. ID. No:22) and AODA2303 primer (SEQ. ID. No:23) to obtain a transcription/translation template. Furthermore, a mutant, wherein the 145th cysteine which was believed to share the center of SARS 3CL protease activity was altered to alanine, pEU-E01-SA3CL$^{pro}$ (C145A) (SEQ. ID. No:3) was constructed by the same method as indicated above.

(2) Cloning of Genetic DNA of Substrate GFP-RS-GUS

While pEU-E01-GUS vector was subjected to Inverse PCR using an antisense primer (SEQ. ID. No:24) comprising E01 and Xho1 sequences and a sense primer (SEQ. ID. No:25) comprising Pst1 sequence and the start codon of GUS, PEU3-GFP vector was subjected to PCR using a sense primer (SEQ. ID. No:26) comprising Xho1 sequence and the start codon of GFP, and a primer (SEQ. ID. No:27) comprising the cleavage site sequence (RS) of SA3CL$^{pro}$ and a portion of GFP sequence. The respective PCR products were extracted with phenol/chloroform and cleaved using Xho1 and Pst1 (from NEB). The cleaved DNA was purified with GENE CLEAN II Kit (from Funakoshi Co., Ltd), the plasmid was circularized by ligation and transformed, the aimed colony was selected in the same manner as in (1) and downsized, and the plasmid {pEU-GFP-RS-GUS (SEQ. ID. No:2)} was amplified in *E. Coli*. Thereafter, to obtain the plasmid alone, it was purified using GenElute™ Plasmid Miniprep Kit (from SIGMA). The obtained pEU-E01-GUS vector was subjected to PCR using SPu primer and AODA2303 primer.

(3) Cloning of Fusion Gene from GFP-RS-SA3CL$^{pro}$ and GFP-RS-SA3CL$^{pro}$ (C145A)

PCR was carried out using pBS-SA3L$^{pro}$ plasmid as a template, RS-SA3L$^{pro}$-S1 (SEQ. ID. No:28), which was a sense primer comprising Pst1 site and a portion of RS sequence, and M13 primer (SEQ. ID. No:29). This PCR product was extracted with phenol/chloroform and cleaved with restriction enzymes, Pst1 (from NEB) and BamH1 (from NEB). Further, GFP-RS-GUS plasmid was cleaved with Pst1 (from NEB) and BamH1 (from NEB) in the same manner. These two kinds of cleaved DNAs were purified with GENE CLEAN 2 Kit (from Funakoshi Co., Ltd), the plasmid was circularized by ligation and transformed, the aimed colony was selected in the same manner as in (1) and downsized, and this plasmid was amplified in *E. Coli*. Thereafter, to obtain plasmid {pEU-GFP-RS-SA3CL$^{pro}$ (SEQ. ID. No:5)} alone, it was purified using GenElute™ Plasmid MinipreKit (from SIGMA). The obtained GFP-RS-SA3CL$^{pro}$ vector was subjected to PCR using SPu primer, AODA2303 primer. Furthermore, GFP-RS-SA3CL$^{pro}$ (C145A) was constructed by inserting mutant SA3CL$^{pro}$ (C145A), wherein the 145th cysteine which was also believed to share the center of SARS 3CL protease activity was altered to alanine.

(4) Cloning of GST-RS-SA3CL$^{pro}$ Fusion Gene

PCR was conducted using pEU-E01-GSTN2 plasmid as a template, GST-RS-SA3L$^{pro}$sen (SEQ. ID. No:30), which was a sense primer comprising Xho1 site and the start codon of GST, and GST-RS-SA3L$^{pro}$ anti (SEQ. ID. No:31) which was an antisense primer comprising Pst 1 site and a portion of GST sequence. This PCR product was extracted with phenol/chloroform and cleaved with restriction enzyme, Xho 1 (from NEB) and Pst 1 (from NEB). Further, GFP-RS-GUS plasmid was cleaved with Pst1 (from NEB) and BamH 1 (from NEB) in the same manner. These two kinds of DNAs was purified with GENE CLEAN 2 Kit (from Funakoshi Co., Ltd), the plasmid was circularized by ligation and transformed, the aimed colony was selected in the same manner as in (1) and downsized, and this plasmid {pEU-GST-RS-SA3CL$^{pro}$ (SEQ. ID. No:4)} was amplified in *E. Coli*. Thereafter, to obtain the plasmid alone, it was purified using GenElute™ Plasmid MinipreKit (from SIGMA). The obtained GST-RS-SA3CL$^{pro}$ vector was subjected to PCR using Spu primer, AODA2303 primer.

(5) Preparation of Wheat Embryo Extract Solution

The seeds of Chiho wheat produced in Hokkaido and/or those of Chikugoizumi wheat produced in Ehime were fed into the mill (from Fritsch: Rotor Speed Mill pulverisette Type 14) at a rate of 100 g/min. and pulverized gently at a speed of 8,000 rpm. After collecting a fraction containing wheat embryo having germinability with a sieve (sieve opening from 0.7 to 1.00 mm), selection by flotation with the mixture of carbon tetrachloride and cyclohexane (volume ratio: carbon tetrachloride: cyclohexane=2.4:1) was conducted to recover a floating fraction containing wheat embryo having germinability, then organic solvents were evaporated to remove at room temperature, and then mixed impurities such as seed coats were removed by blowing at room temperature to obtain a crude wheat embryo fraction. Wheat embryo was determined in this crude wheat embryo fraction by visual inspection and sorted out with a bamboo rod. The obtained wheat embryo fraction was suspended in distilled water at 4° C., and washed with a wash solution in the ultrasonic cleaner until white color became clear. Then, it was suspended in 0.5 v % solution of Nonidet (from Nacalai Techtonics) P40 and washed with a wash solution in the ultrasonic cleaner until white color became clear to obtain wheat embryo. The preparation of a wheat embryo extract-containing solution was conducted in accordance with a conventional method (Erickson, A. H. et al., (1996) Meth. In Enzymol., 96, 38-50). The following operations were conducted at 4° C. First, wheat embryo frozen with liquid nitrogen was finely ground in a mortar. 1 ml of an extraction solvent prepared by the partial modification of Pattersons' method per 1 g of the obtained powder, 80 mM of HEPES-KOH (pH 7.6), 200 mM of potassium acetate, 2 mM of magnesium acetate, 4 mM of calcium chloride, and 0.6 mM of each 20 kinds of L-amino acids, and 8 mM of threitol (respectively) were added to obtain their respective final concentrations, and then stirred carefully without developing foam. A supernatant obtained by centrifugation at 30,000×g for 15 min. was recovered as wheat embryo extract solution and subjected to gel filtration with Sephadex G-25 column (from Amerham Pharmacia Biotech), which was previously equilibrated with a solution whose final concentrations were (respectively) as follows: 40 mM of HEPES-KOH (p) 7.6, 100 mM of potassium acetate, 5 mM of magnesium acetate, 0.3 mM of each 20 kinds of L-amino acids, and 4 mM of threitol. The concentration of a wheat embryo extract-containing solution thus obtained was adjusted to have an optical density (O.D.) (A260) 170 to 250 (A260/A280=1.5) at 260 nm.

(6) Fabrication of Translation Template

The PCR products cloned in (1), (2), (3) and (4) were used respectively as a transcription template for in vitro transcription. For transcription, 25 μl of reaction system was prepared to have a final concentration of as follows respectively: 80 mM of Hepes-KOH, 16 mM of magnesium acetate, 2 mM of spermidine (from Nacalai Techtonics), 10 mM of DTT, 3 mM of NTP (from Wako Pure Chemical Industries, Ltd.), 1 U/μl of SP6 RNA polymerase, 1 U/μl of Rnase Inhibitor (from TAKARA) and the 10% PCR product. These reaction solutions were incubated for three hours at 37° C., and then the mRNAs {SA3CL$^{pro}$, SA3CL$^{pro}$ (C145A), GFP-RS-GUS, GFP-RS-SA3CL$^{pro}$, GST-RS-SA3CL$^{pro}$} were purified by ethanol precipitation.

(7) Protein Synthesis Using Cell-free Protein Synthesis System Using Wheat Embryo Extract Solution (Bilayer System)

Proteins (GFP-RS-GUS, GFP-RS-SA3CL$^{pro}$ and GST-RS-SA3CL$^{pro}$) were synthesized using a bilayer system. First, 125 μl of the external solution for dialysis (the respective final concentrations were as follows: 30 mM of HEPES-KOH (pH 7.8), 100 mM of potassium acetate, 2.7 mM of magnesium acetate, 0.4 mM of spermidine (from Nacalai Techtonics), 0.25 mM of each 20 kinds of L-amino acids, 2.5 mM of threitol, 1.2 mM of ATP, 0.25 mM of GTP, 16 mM of phosphocreatine (from Wako Pure Chemical Industries, Ltd.)) was placed into a microtiter plate, the wheat embryo extract-containing solution prepared in (5) indicated above was added to provide a reaction solution for protein synthesis to have a final optical density (O.D.) (A260) of 60 (the final concentrations were respectively as follows: 30 mM of HEPES-KOH (pH 7.8), 100 mM of potassium acetate, 2.7 mM of magnesium acetate, 0.4 mM of spermidine (from Nacalai Techtonics), 0.25 mM of each 20 kinds of L-amino acids, 2.5 mM of threitol, 1.2 mM of ATP, 0.25 mM of GTP, 16 mM of phosphocreatine (from Wako Pure Chemical Industries, Ltd.) and 400 μg/ml of creatine kinase (from Roche)), and in 25 μl of this solution, the mRNAs (GFP-RS-GUS, GFP-RS-SA3CL$^{pro}$ and GST-RS-SA3CL$^{pro}$) prepared in (6) indicated above were suspended, overlaid without disrupting the boundary surface of the reaction solution for protein synthesis, and incubated for 18 hours at 26° C. to conduct protein synthesis.

(8) Protein Synthesis Using Cell-Free Protein Synthesis System Using Wheat Embryo Extract Solution (Dialysis)

Proteins {SA3CL$^{pro}$ and SA3CL$^{pro}$ (C145A)} were synthesized through dialysis. 50 μl of the wheat embryo extract-containing solution used in (5) was added into dialysis cup MWCO 12000 (from Bio Tech), 700 μl of the external solution for dialysis was placed into Maruemu™ container (the final concentrations of both the wheat embryo extract-containing solution and external solution for dialysis, were same as those in (7)), and then incubated for a day at 26° C. with supplying proteins' substrates, amino acids, ATP and the like for energy source to conduct protein synthesis.

(9) RS Sequence Cleavage by SARS 3CL Protease and Activity Detection

SA3CL$^{pro}$ and SA3CL$^{pro}$ (C145A) synthesized by dialysis (8) and the protein of GFP-RS-GUS, which was labeled with $^{14}$C-Leu by bilayer system (7), (the final concentration of $^{14}$C-Leu was 20 μCi/μl) were mixed in their equal amounts and incubated for two hours at 37° C. (FIG. 1A). Thereafter, to this mixture, Sample Buffer (the final concentrations were respectively as follows: 50 mM of Tris-HCl (pH 6.8), 2% sodium dodecyl sulphate, 1% β-mercaptoethanol, 10% glycerol and 0.2% BPB (from Nacalai Techtonics)) was added, and the resultant was heated at 98° C. for 5 minutes followed by cooling rapidly with ice-cold water. This sample was subjected to SDS-PAGE using 12.5% SDS gel at 25 mA for 80 minutes. The RI-labeled protein was detected using an imaging plate and BAS-2500 (from Fuji Photo Film Co., Ltd.) (FIG. 1B). Further, after the protein synthesis of SA3CL$^{pro}$ and GFP-RS-GUS by dialysis, they were mixed in their equal amounts to perform Native PAGE, and the fluorescence was detected by Dark Reader (from BM Equipment Co., Ltd.) (FIG. 2)

Referring to FIG. 1B. SA3CL$^{pro}$ was cleaved within a cleavage site {RS (PPQTSITSAVLQ↓SGFRKMAFPSGKV)} (SEQ ID NO: 33) of the linker between GFP and GUS, but mutant SA3CL$^{pro}$ (C145A) was not cleaved. Further, it was found that fluorescent substance GFP had a nature that its fluorescence intensity would become remarkably intensified by cleavage. Referring to FIG. 2, it was shown that the increase of concentration of SA3CL$^{pro}$ intensified GFP fluorescence intensity which showed the amount of GFP-RS-GUS cleaved. From this, it was found that as SA3CL$^{pro}$ activity was proportional to GFP fluorescence intensity, the inhibitory effect of a candidate drug capable of inhibiting the activity of a bioactive protein could be measured by fluorescence intensities.

(10) Detection of Autolysis Activity by SA3CL$^{pro}$ from GST-RS-SA3CL$^{pro}$ and GFP-RS-SA3CL$^{pro}$ To 10 μl of synthesis solutions of GFP-RS-SA3CL$^{pro}$ and GST-RS-SA3CL$^{pro}$ (the final concentration of $^{14}$C-Leu was 12 μCi/μl) both of which were labeled with $^{14}$C-Leu by bilayer system (7), 5 μl of 3× Sample Buffer was mixed (FIG. 3A, FIG. 4A) to detect RI-labeled protein as described in (9) (FIG. 3B, FIG. 4B). As a method for detecting GST-RS-3CL$^{pro}$, on the initiation of synthesis, the sample of GST-RS-3CL$^{pro}$ was collected every minutes, separated on SDS-PAGE, and then autoradiographically examined. Further, as a method for detecting GFP-RS-SA3CL$^{pro}$, the sample was collected after 20 hours of reaction, separated on SDS-PAGE, and autoradiographically examined (FIG. 4B) GFP-RS-SA3CL$^{pro}$ and GFP-RS-SA3CL$^{pro}$ (C145A) were synthesized by bilayer system, subjected to Native PAGE, and the fluorescence was detected by Dark Reader (from BM Equipment Co., Ltd.) (FIG. 5).

Referring to FIG. 3B, autocleavage was found to occur in the cleavage site (RS) which had been designed to position in the linker part between SA3CL$^{pro}$ itself and GST fused to its N-terminal end. Furthermore, within 30 minutes after the initiation of synthesis of GST-RS-SA3CL$^{pro}$, it was found that SA3CL$^{pro}$ cleaved the RS positioned between GST and itself. From this, it was found that even in the folding process wherein SA3CL$^{pro}$ had not become a fully matured protein (finished folding), the protein's autodigestion had already occurred. Referring to FIG. 4B, it was found that SA3CL$^{pro}$'s autocleavage occurred not only in cleavage site (RS) designed to position in the linker part between SA3CL$^{pro}$ itself and GFP fused to its N-terminal end, but the products cleaved in sites other than the original cleavage site (RS) were detected (an arrow in the figure). Referring to FIG. 5, while SA3CL$^{pro}$ was cleaved in cleavage site (RS) in the linker between GFP and itself, mutant SA3CL$^{pro}$ (C145A) was not cleaved. From this combined with the results of FIG. 1B, it was found that in a cell-free system with the use of a wheat embryo extract solution according to the present invention, bioactive proteins such as SA3CL$^{pro}$ could be synthesized in a native state with sustaining its activity. Further, it was found that as SA3CL$^{pro}$ was cleaved in the same manner as in FIG. 2, GFP's fluorescence intensity was intensified, and further SA3CL$^{pro}$'s activity was proportional to GFP fluorescence intensity, thereby the inhibitory effect of a candidate drug capable of inhibiting the activity of a bioactive protein could be measured by fluorescence intensities.

From the results described above, it was found that the sensibility of protease activity of SA3CL$^{pro}$ was different between during the folding process and after the termination of folding. Namely, protein synthesis in a cell-free synthesis system, after the initiation of synthesis, comprises also a protein on the way to folding, which sustains its activity as protease in spite of its incomplete folding, but it is suggested that the cleavage may occur at a position other than the original cleavage sites. In other words, it is believed that within an actual cell (in vivo), there may exist a bioactive protein which is on an incomplete folding of state but has a different cleavage site from the normal to sustain protease activity.

EXAMPLE 2

Screening for Inhibitor Candidate to SARS Protease (1) Synthesis by Bilayer System Using SARS Protease and Substrate Protein Protein synthesis was conducted in accordance with a method described in EXAMPLE 1 (7) using SARS protease (SA3CL$^{pro}$), a mutant thereof (SA3CL$^{pro}$ (C145A)) and the translation template of substrate GFP-RS-GUS described in EXAMPLE 1 (6). Herein, the final optical density (OD260) of a wheat embryo extract-containing solution was set to 120 and the final concentration of creatine kinase to 40 ng/μl. Further, synthesis reaction was conducted for 20 hours at 26° C. with the upper layer set to 206 μl in amount of reaction solution and the lower layer to 20 μl.

(2) Assay of Inhibitor Candidate

Each inhibitor candidate A and B was dissolved in 10% DMSO. Herein, inhibitor candidate A was a commercially available compound library from ASINEX Ltd., the accession No. AST6748415. Inhibitor Candidate B was a low molecular compound. 1 μl of SA3CL$^{pro}$ synthesis reaction solution described in the preceding paragraph (1), 3 μl of translation buffer (see EXAMPLE 1), 1 μl of 10% DMSO solution of each candidate A and B (Lane 3, Lane 4) (for control, 10% DMSO solution alone: Lane 2) were mixed. In addition, for negative control, in place of SA3CL$^{pro}$, a mixture of 1 μl of SA3CL$^{pro}$ (C145A) synthesis reaction solution, 3 μl of translation reaction solution and 1 μl of 10% DMSO solution (Lane 5) was used. After preincubating them for 10 minutes at 37° C., 5 μl of GFP-RS-GUS synthesis reaction solution described in the preceding paragraph (1) was added and reacted for an hour at 37° C. Each reaction solution was analyzed by 12.5% Native PAGE and subjected to detection of the fluorescence intensity of GFP using Molecular Imager FXPro (from BioRad).

The assay results of the inhibitor candidates were presented in FIG. 6. In control (Lane 2), along with GFP-RS-GUS's band, GFP's band which was produced by SA3CL$^{pro}$ protease activity was also detected. SA3CL$^{pro}$ (C145A), which was used in negative control (Lane 5) and the mutant of the major responsible for protease activity, produced significantly less GFP because of the decreased protease activity. In the case of inhibitor candidate A (Lane 3) added, the production levels of GUS and GFP were observed to be as much as that of positive control (Lane 2), thereby it is believed that this compound may not have an inhibitory activity to SA3CL$^{pro}$ protease activity. In the case of inhibitor candidate B (Lane 4) added, GFP's band became weaker than that of positive control (Lane 2), therefore the fact that this compound had an inhibitory activity to SA3CL$^{pro}$ protease activity was presented. Then, Lane 1 was a fraction containing GFP-RS-GUS alone.

From the results described above, the method for searching a drug to a bioactive protein using a cell-free protein synthesis means with the use of a wheat embryo extract of the present invention allowed screening for an inhibitor candidate to SARS protease activity.

In a conventional screening system, mainly matured proteins after finishing folding were aimed. However, the system for screening a candidate drug to a protease on the folding process according to the present invention is a new system which has not been aimed by conventional screenings, and therefore it may be considered novel and useful. Furthermore, the screening system according to the present invention allows a means for screening a candidate drug which has reactivity to the structure or the function of a protein in the translation process, a protein in the autodigestion reaction process, a protein in the substrate recognition reaction process, and a protein in the folding reaction process, besides conventional matured proteins.

This application claims priority from Japan Patent Serial No. 2003-316081, which is incorporated herein by reference.

SEQUENCE LISTING

<160> NUMBER OF SEQ ID NOS: 32

Figure 1:
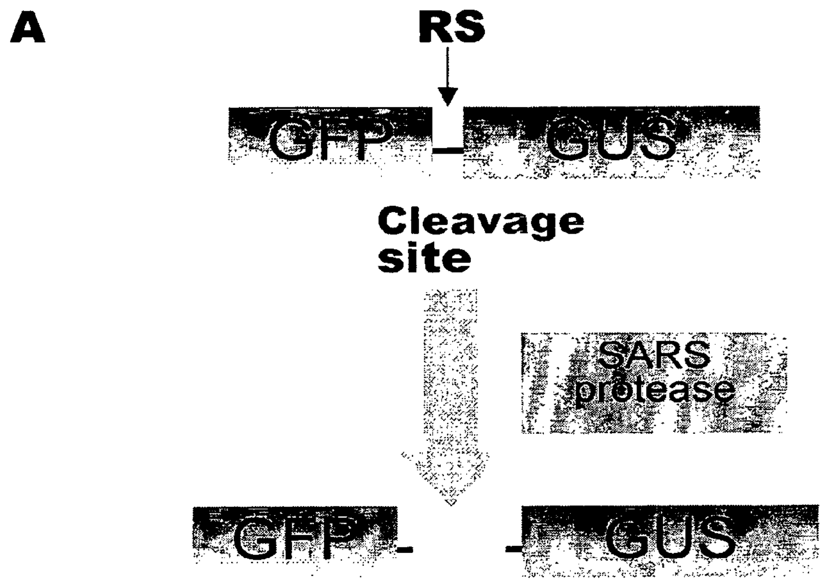
FIG. 1A is a schematic representation of SARS protease ($3CL^{pro}$), which is cleaving GFP-RS-GUS (substrate)
FIG. 1B is a figure of SDS-PAGE showing $SA3CL^{pro}$ activity.
Figure 1:
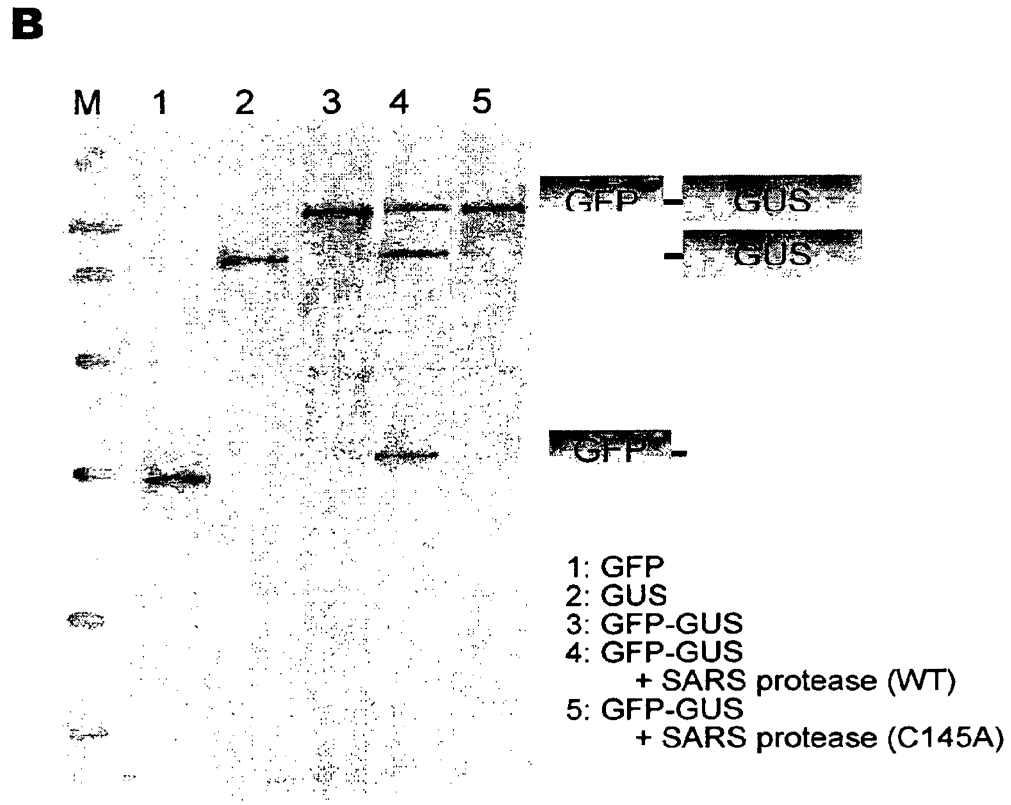
Figure 2:
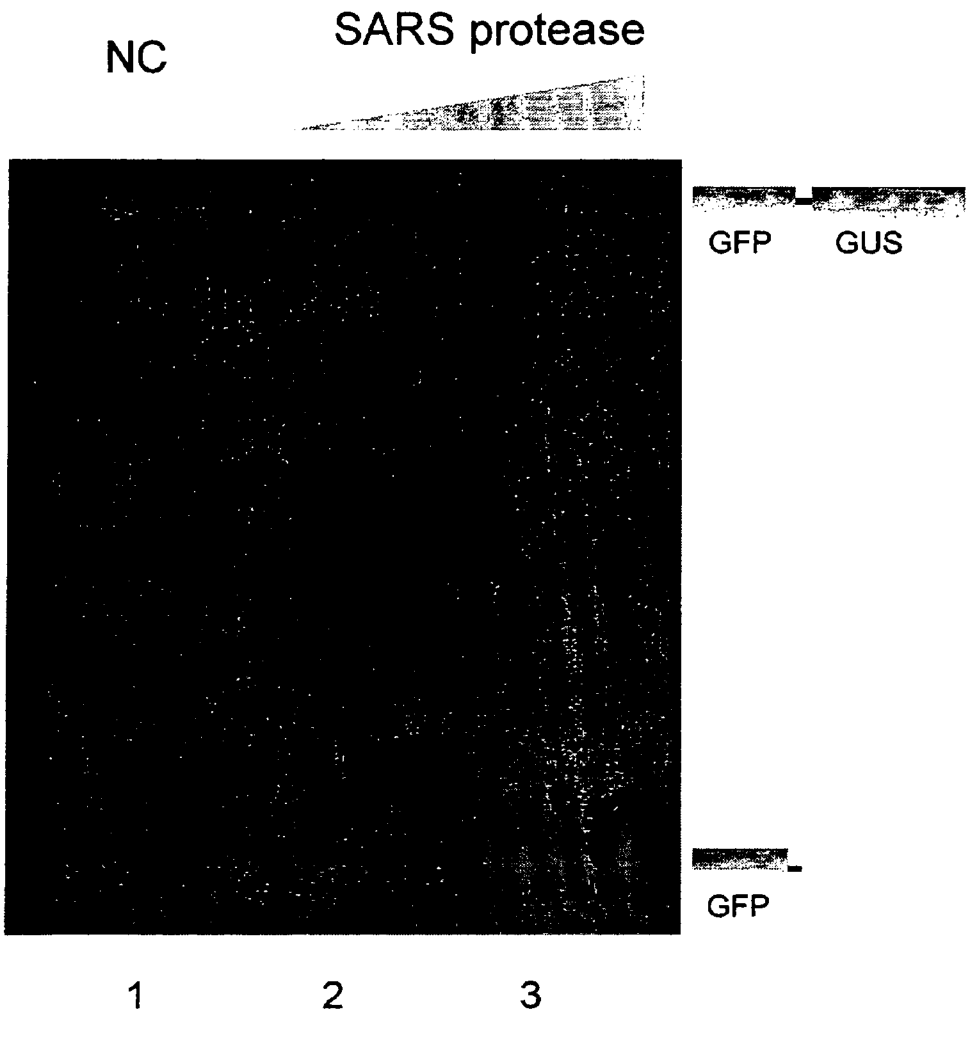
FIG. 2 is a figure of Native PAGE showing the differences in fluorescence intensity between before and after the GFP-GUS cleavage.
Figure 3:
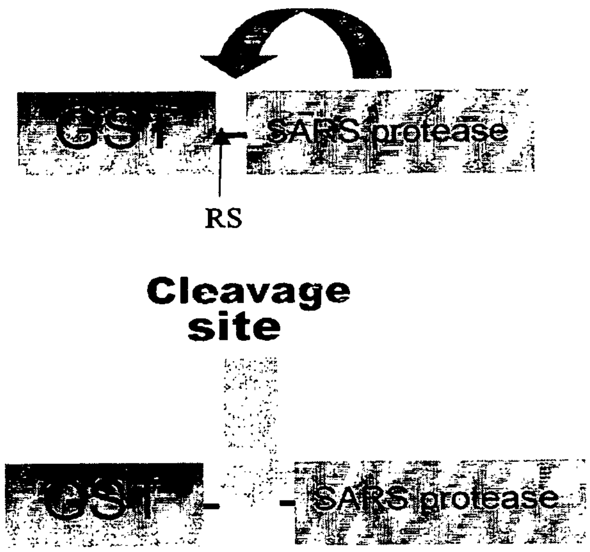
FIG. 3A is a schematic representation of SARS protease ($3CL^{pro}$) autocleavaging the cleavage site designed, wherein the protease was positioned at a knot connecting to GST, which was fused to the N-terminal of itself.
FIG. 3B is a figure of autoradiogram showing a fragment cleaved with GST-$3CL^{pro}$ synthesized.
Figure 3:
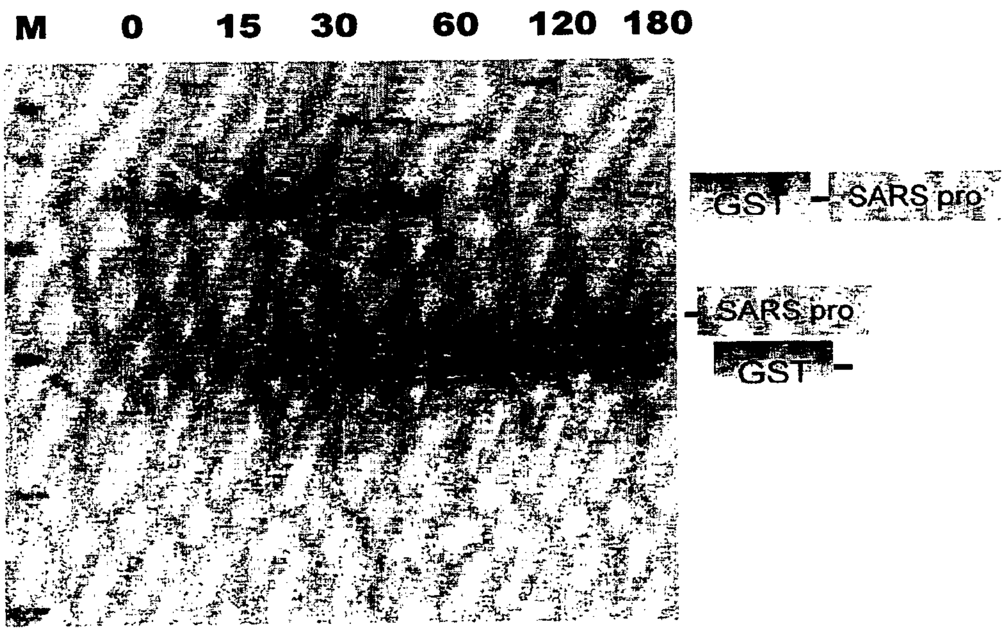
Figure 4:
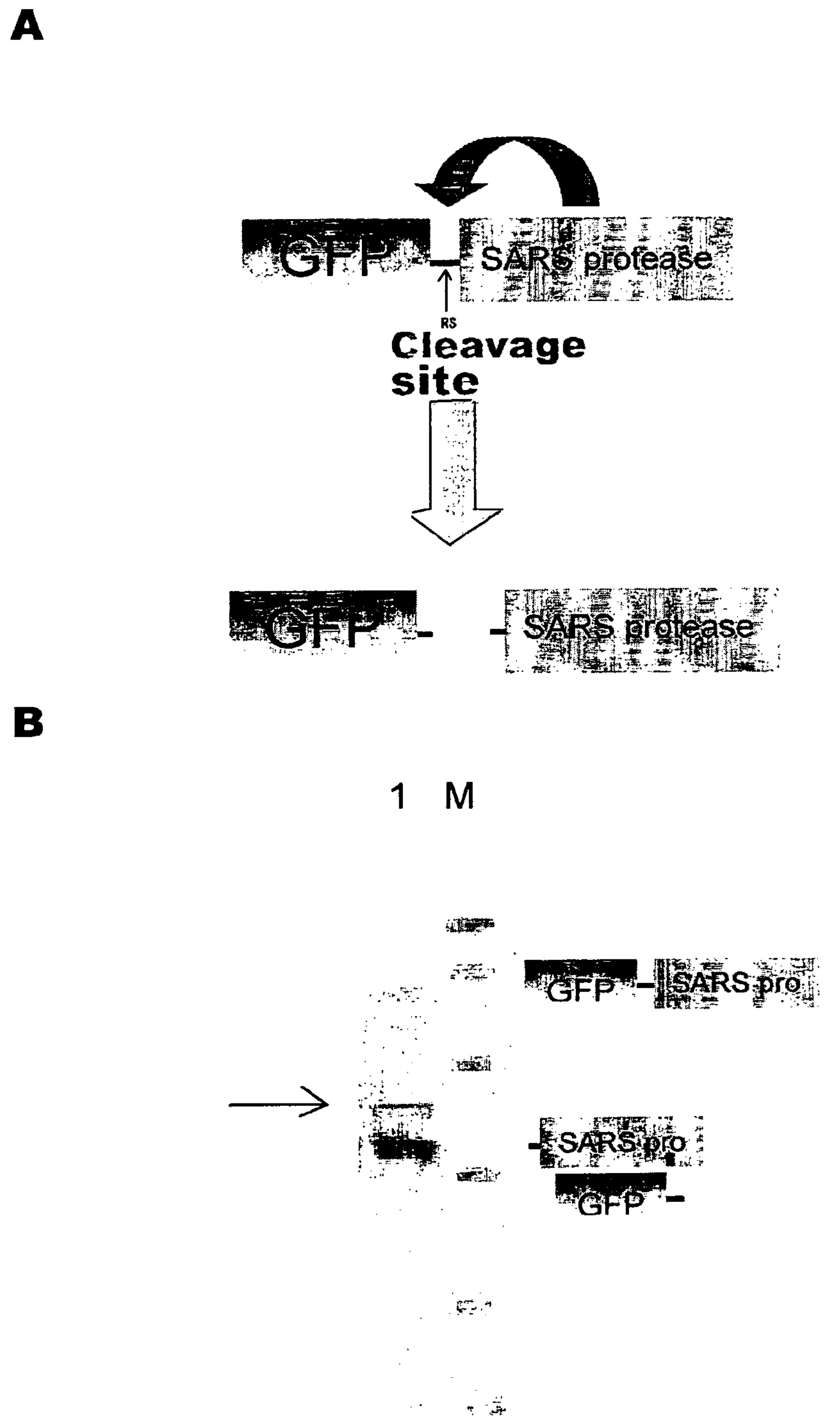
FIG. 4A is a schematic representation of SARS protease ($3CL^{pro}$) cleaving GFP which was fused to the N-terminal of the protease itself.
FIG. 4B is a figure of autoradiogram showing a fragment cleaved with GFP-$3CL^{pro}$ synthesized.
Figure 5:
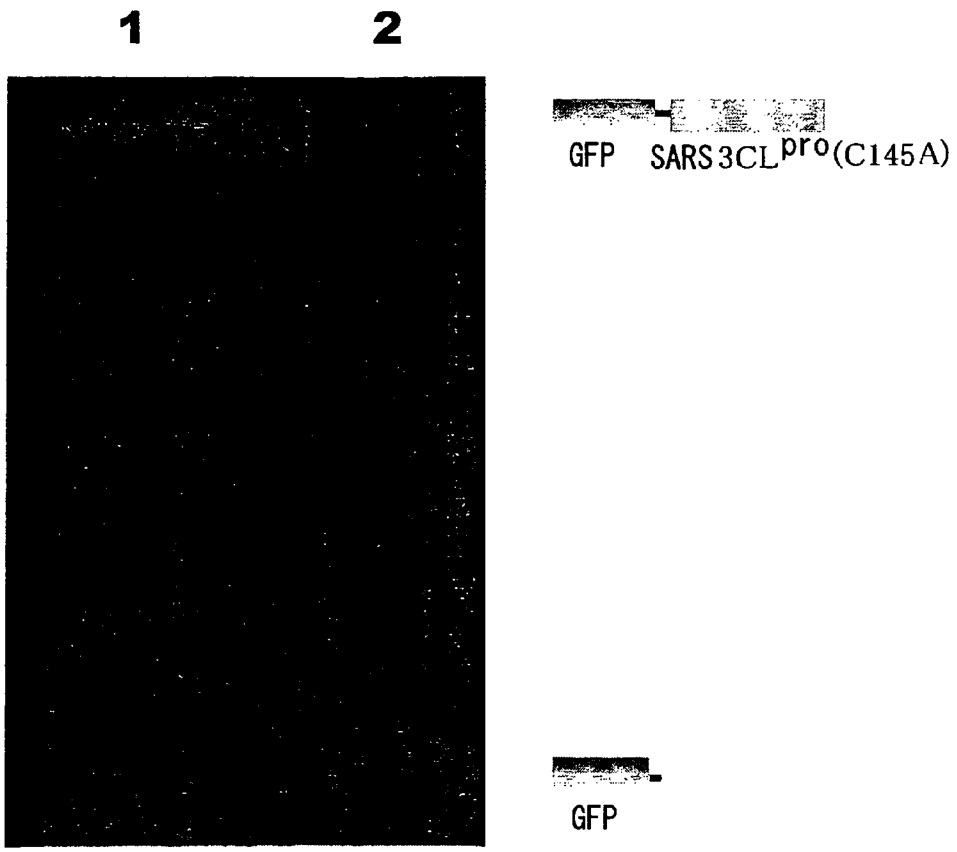
FIG. 5 is a figure showing changes in fluorescence intensity by the inhibition of autolysis.
Figure 6:
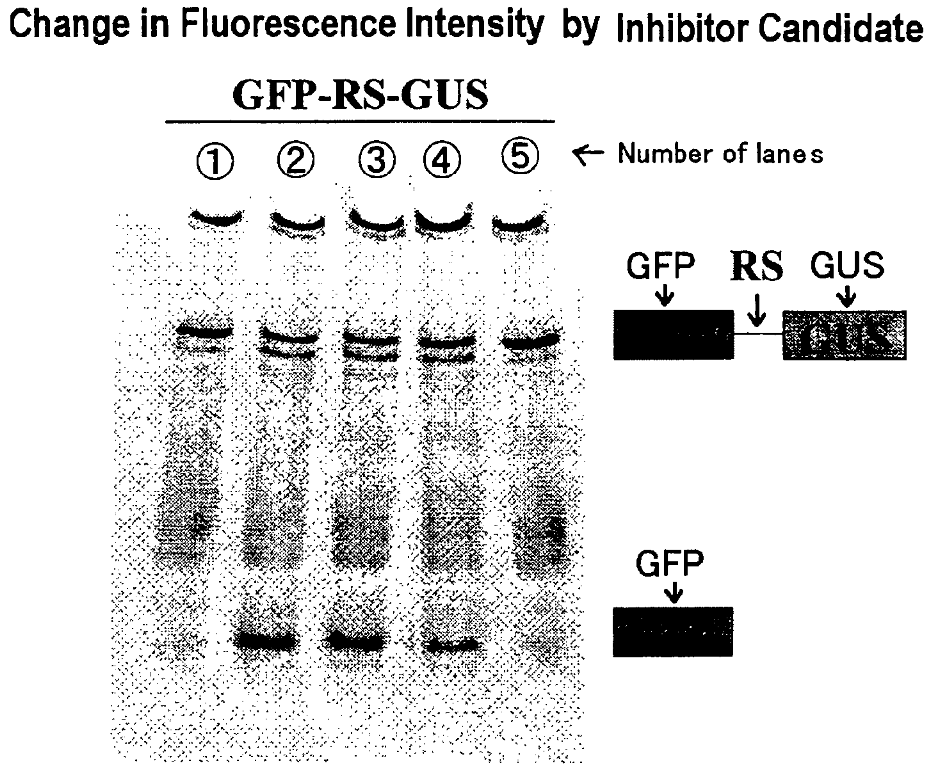
FIG. 6 is a figure showing changes in fluorescence intensity by an inhibitor candidate.

<210> SEQ ID NO 1
<211> LENGTH: 4608
<212> TYPE: DNA
<213> ORGANISM: Human coronavirus

<400> SEQUENCE: 1
atttaggtga cactatagaa ctcacctatc tccccaacac ctaataacat tcaatcactc 60
tttccactaa ccacctatct acatcaccaa gatatcacta gttctcgaga tgagcggctt 120
ccgcaagatg gccttcccca gcggcaaggt cgagggctgc atggtgcagg tcacctgcgg 180
caccactacc ctgaacggcc tgtggctgga tgacaccgtc tactgccccc gccacgtgat 240
ctgcaccgcc gaggacatgc tgaaccccaa ctacgaggac ctgctcatcc gcaagagcaa 300
ccactccttc ctggtgcagg ccggcaacgt ccagctgcgc gtgatcggcc acagcatgca 360
gaactgcctg ctccgcctga aggtggacac cagcaacccc aagaccccca agtacaagtt 420
cgtgcgcatc cagcccggcc agaccttcag cgtgctggcc tgctacaacg gcagccccag 480
cggcgtgtac cagtgcgcca tgcgccccaa ccacaccatc aagggcagct tcctgaacgg 540
gagctgcggc agcgtgggct tcaacatcga ctacgactgc gtaagcttct gctacatgca 600
ccacatggag ctgcccaccg gcgtgcacgc cggcaccgac ctggagggca agttctacgg 660
ccccttcgtg gaccgccaga ccgcccaggc cgccggcacc gacaccacca tcaccctgaa 720
cgtgctggcc tggctgtacg ccgccgtgat caacggcgac cgctggttcc tgaaccgctt 780
caccactacc ctgaacgact tcaacctggt ggccatgaag tacaactacg agcccctgac 840
ccaggaccac gtggacatcc tgggccccct gagcgcccag accggcatcg ccgtcctgga 900
catgtgcgcc gccctgaagg agctgctcca gaacggcatg aacggccgca ccatcctggg 960
cagcaccatc ctggaggacg agttcacccc cttcgacgtc gtgcgccagt gcagcggcgt 1020
gaccttccag taaggatcca tatatagggc ccgggttata attacctcag gtcgacgtcc 1080
catggttttg tatagaattt acggctagcg ccggatgcga cgccggtcgc gtcttatccg 1140
gccttcctat atcaggctgt gtttaagacg ccgccgcttc gcccaaatcc ttatgccggt 1200
tcgacggctg gacaaaatac tgtttatctt cccagcgcag gcaggttaat gtaccacccc 1260
agcagcagcc ggtatccagc gcgtatatac cttccggcgt acctttgccc tccagcgatg 1320

-continued

```
cccagtgacc aaaggcgatg ctgtattctt cagcgacagg gccaggaatc gcaaaccacg   1380
gtttcagtgg ggcaggggcc tcttccggcg attcttacta gctagtatgc ataggtgctg   1440
aaatataaag tttgtgtttc taaaacacac gtggtacgta cgataacgta cagtgttttt   1500
ccctccactt aaatcgaagg gtagtgtctt ggagcgcgcg gagtaaacat atatggttca   1560
tatatgtccg taggcacgta aaaaaagcga gggattcgaa ttcccccgga acccccggtt   1620
ggggcccacg cctcgatcga gcaaaaaaaa aaaaaaaaaa aaaaaaaaaa aaaaaagctt   1680
ggcgtaatca tggtcatagc tgtttcctgt gtgaaattgt tatccgctca caattccaca   1740
caacatacga gccggaagca taaagtgtaa agcctggggt gcctaatgag tgagctaact   1800
cacattaatt gcgttgcgct cactgcccgc tttccagtcg ggaaacctgt cgtgccagct   1860
gcattaatga atcggccaac gcgcggggag aggcggtttg cgtattgggc gctcttccgc   1920
ttcctcgctc actgactcgc tgcgctcggt cgttcggctg cggcgagcgg tatcagctca   1980
ctcaaaggcg gtaatacggt tatccacaga atcaggggat aacgcaggaa agaacatgtg   2040
agcaaaaggc cagcaaaagg ccaggaaccg taaaaaggcc gcgttgctgg cgtttttcca   2100
taggctccgc ccccctgacg agcatcacaa aaatcgacgc tcaagtcaga ggtggcgaaa   2160
cccgacagga ctataaagat accaggcgtt tccccctgga agctccctcg tgcgctctcc   2220
tgttccgacc ctgccgctta ccggatacct gtccgccttt ctcccttcgg gaagcgtggc   2280
gctttctcat agctcacgct gtaggtatct cagttcggtg taggtcgttc gctccaagct   2340
gggctgtgtg cacgaacccc ccgttcagcc cgaccgctgc gccttatccg gtaactatcg   2400
tcttgagtcc aacccggtaa gacacgactt atcgccactg gcagcagcca ctggtaacag   2460
gattagcaga gcgaggtatg taggcggtgc tacagagttc ttgaagtggt ggcctaacta   2520
cggctacact agaaggacag tatttggtat ctgcgctctg ctgaagccag ttaccttcgg   2580
aaaaagagtt ggtagctctt gatccggcaa acaaaccacc gctggtagcg gtggtttttt   2640
tgtttgcaag cagcagatta cgcgcagaaa aaaaggatct caagaagatc ctttgatctt   2700
ttctacgggg tctgacgctc agtggaacga aaactcacgt taagggattt tggtcatgag   2760
attatcaaaa aggatcttca cctagatcct tttaaattaa aaatgaagtt ttaaatcaat   2820
ctaaagtata tatgagtaaa cttggtctga cagttaccaa tgcttaatca gtgaggcacc   2880
tatctcagcg atctgtctat ttcgttcatc catagttgcc tgactccccg tcgtgtagat   2940
aactacgata cgggagggct taccatctgg ccccagtgct gcaatgatac cgcgagaccc   3000
acgctcaccg gctccagatt tatcagcaat aaaccagcca gccggaaggg ccgagcgcag   3060
aagtggtcct gcaactttat ccgcctccat ccagtctatt aattgttgcc gggaagctag   3120
agtaagtagt tcgccagtta atagtttgcg caacgttgtt gccattgcta caggcatcgt   3180
ggtgtcacgc tcgtcgtttg gtatggcttc attcagctcc ggttcccaac gatcaaggcg   3240
agttacatga tcccccatgt tgtgcaaaaa agcggttagc tccttcggtc ctccgatcgt   3300
tgtcagaagt aagttggccg cagtgttatc actcatggtt atggcagcac tgcataattc   3360
tcttactgtc atgccatccg taagatgctt ttctgtgact ggtgagtact caaccaagtc   3420
attctgagaa tagtgtatgc ggcgaccgag ttgctcttgc ccggcgtcaa tacgggataa   3480
taccgcgcca catagcagaa ctttaaaagt gctcatcatt ggaaaacgtt cttcggggcg   3540
aaaactctca aggatcttac cgctgttgag atccagttcg atgtaaccca ctcgtgcacc   3600
caactgatct tcagcatctt ttactttcac cagcgtttct gggtgagcaa aaacaggaag   3660
```

-continued

```
gcaaaatgcc gcaaaaaagg gaataagggc gacacggaaa tgttgaatac tcatactctt   3720

cctttttcaa tattattgaa gcatttatca gggttattgt ctcatgagcg gatacatatt   3780

tgaatgtatt tagaaaaata aacaaatagg ggttccgcgc acatttcccc gaaaagtgcc   3840

acctgacgtc taagaaacca ttattatcat gacattaacc tataaaaata ggcgtatcac   3900

gaggcccttt cgtctcgcgc gtttcggtga tgacggtgaa aacctctgac acatgcagct   3960

cccggagacg gtcacagctt gtctgtaagc ggatgccggg agcagacaag cccgtcaggg   4020

cgcgtcagcg ggtgttggcg ggtgtcgggg ctggcttaac tatgcggcat cagagcagat   4080

tgtactgaga gtgcaccata tcgacgctct cccttatgcg actcctgcat taggaagcag   4140

cccagtagta ggttgaggcc gttgagcacc gccgccgcaa ggaatggtgc atgcaaggag   4200

atggcgccca acagtccccc ggccacgggg cctgccacca tacccacgcc gaaacaagcg   4260

ctcatgagcc cgaagtggcg agcccgatct tccccatcgg tgatgtcggc gatataggcg   4320

ccagcaaccg cacctgtggc gccggtgatg ccggccacga tgcgtccggc gtagaggatc   4380

tggctagcga tgaccctgct gattggttcg ctgaccattt ccggggtgcg gaacggcgtt   4440

accagaaact cagaaggttc gtccaaccaa accgactctg acggcagttt acgagagaga   4500

tgatagggtc tgcttcagta agccagatgc tacacaatta ggcttgtaca tattgtcgtt   4560

agaacgcggc tacaattaat acataacctt atgtatcata cacatacg               4608
```

<210> SEQ ID NO 2
<211> LENGTH: 6389
<212> TYPE: DNA
<213> ORGANISM: Artificial
<220> FEATURE:
<223> OTHER INFORMATION: pEU-GFP-RS-GUS

<400> SEQUENCE: 2

```
atttaggtga cactatagaa ctcacctatc tccccaacac ctaataacat tcaatcactc     60

tttccactaa ccacctatct acatcaccaa gatatcactc gagaatggtg agcaagggcg    120

aggagctgtt caccggggtg gtgcccatcc tggtcgagct ggacggcgac gtgaacggcc    180

acaagttcag cgtgtccggc gagggcgagg gcgatgccac ctacggcaag ctgaccctga    240

agttcatctg caccaccggc aagctgcccg tgccctggcc caccctcgtg accaccttca    300

cctacggcgt gcagtgcttc agccgctacc ccgaccacat gaagcagcac gacttcttca    360

agtccgccat gcccgaaggc tacgtccagg agcgcaccat cttcttcaag gacgacggca    420

actacaagac ccgcgccgag gtgaagttcg agggcgacac cctggtgaac cgcatcgagc    480

tgaagggcat cgacttcaag gaggacggca acatcctggg gcacaagctg gagtacaact    540

acaacagcca caacgtctat atcatggccg acaagcagaa gaacggcatc aaggtgaact    600

tcaagatccg ccacaacatc gaggacggca gcgtgcagct cgccgaccac taccagcaga    660

acacccccat cggcgacggc cccgtgctgc tgcccgacaa ccactacctg agcacccagt    720

ccgccctgag caaagacccc aacgagaagc gcgatcacat ggtcctgctg gagttcgtga    780

ccgccgccgg gatcactcac ggcatggacg agctgtacaa gcccccccag accagcatca    840

cctctgccgt gctgcagagc ggcttccgca agatggcctt ccccagcggc aaggtgatgt    900

tacgtcctgt agaaacccca acccgtgaaa tcaaaaaact cgacggcctg tgggcattca    960

gtctggatcg cgaaaactgt ggaattgatc agcgttggtg ggaaagcgcg ttacaagaaa   1020

gccgggcaat tgctgtgcca ggcagtttta acgatcagtt cgccgatgca gatattcgta   1080

attatgcggg caacgtctgg tatcagcgcg aagtctttat accgaaaggt tgggcaggcc   1140
```

-continued

```
agcgtatcgt gctgcgtttc gatgcggtca ctcattacgg caaagtgtgg gtcaataatc   1200
aggaagtgat ggagcatcag ggcggctata cgccatttga agccgatgtc acgccgtatg   1260
ttattgccgg gaaaagtgta cgtatcaccg tttgtgtgaa caacgaactg aactggcaga   1320
ctatcccgcc gggaatggtg attaccgacg aaaacggcaa gaaaaagcag tcttacttcc   1380
atgatttctt taactatgcc ggaatccatc gcagcgtaat gctctacacc acgccgaaca   1440
cctgggtgga cgatatcacc gtggtgacgc atgtcgcgca agactgtaac cacgcgtctg   1500
ttgactggca ggtggtggcc aatggtgatg tcagcgttga actgcgtgat gcggatcaac   1560
aggtggttgc aactggacaa ggcactagcg ggactttgca agtggtgaat ccgcacctct   1620
ggcaaccggg tgaaggttat ctctatgaac tgtgcgtcac agccaaaagc cagacagagt   1680
gtgatatcta cccgcttcgc gtcggcatcc ggtcagtggc agtgaagggc gaacagttcc   1740
tgattaacca caaaccgttc tactttactg gctttggtcg tcatgaagat gcggacttgc   1800
gtggcaaagg attcgataac gtgctgatgg tgcacgacca cgcattaatg gactggattg   1860
gggccaactc ctaccgtacc tcgcattacc cttacgctga agagatgctc gactgggcag   1920
atgaacatgg catcgtggtg attgatgaaa ctgctgctgt cggctttaac ctctctttag   1980
gcattggttt cgaagcgggc aacaagccga aagaactgta cagcgaagag gcagtcaacg   2040
gggaaactca gcaagcgcac ttacaggcga ttaaagagct gatagcgcgt gacaaaaacc   2100
acccaagcgt ggtgatgtgg agtattgcca acgaaccgga tacccgtccg caaggtgcac   2160
gggaatattt cgcgccactg gcggaagcaa cgcgtaaact cgacccgacg cgtccgatca   2220
cctgcgtcaa tgtaatgttc tgcgacgctc acaccgatac catcagcgat ctctttgatg   2280
tgctgtgcct gaaccgttat tacggatggt atgtccaaag cggcgatttg gaaacggcag   2340
agaaggtact ggaaaaagaa cttctggcct ggcaggagaa actgcatcag ccgattatca   2400
tcaccgaata cggcgtggat acgttagccg ggctgcactc aatgtacacc gacatgtgga   2460
gtgaagagta tcagtgtgca tggctggata tgtatcaccg cgtctttgat cgcgtcagcg   2520
ccgtcgtcgg tgaacaggta tggaatttcg ccgattttgc gacctcgcaa ggcatattgc   2580
gcgttggcgg taacaagaaa gggatcttca ctcgcgaccg caaaccgaag tcggcggctt   2640
ttctgctgca aaaacgctgg actggcatga acttcggtga aaaaccgcag cagggaggca   2700
aacaatgaat caacaactct cctggcgcac catcgtcggc tacagcctcg ggaattgcta   2760
ccgagctcgg tacctgtccg cggtcgcgac gtacgcgggc ggccgccata aattggatcc   2820
atatataggg cccgggttat aattacctca ggtcgacgtc ccatggtttt gtatagaatt   2880
tacggctagc gccggatgcg acgccggtcg cgtcttatcc ggccttccta tatcaggctg   2940
tgtttaagac gccgccgctt cgcccaaatc cttatgccgg ttcgacggct ggacaaaata   3000
ctgtttatct tcccagcgca ggcaggttaa tgtaccaccc cagcagcagc cggtatccag   3060
cgcgtatata ccttccggcg tacctttgcc ctccagcgat gcccagtgac caaaggcgat   3120
gctgtattct tcagcgacag ggccaggaat cgcaaaccac ggtttcagtg gggcaggggc   3180
ctcttccggc gattcttact agctagtatg cataggtgct gaaatataaa gtttgtgttt   3240
ctaaaacaca cgtggtacgt acgataacgt acagtgtttt tccctccact taaatcgaag   3300
ggtagtgtct tggagcgcgc ggagtaaaca tatatggttc atatatgtcc gtaggcacgt   3360
aaaaaaagcg agggattcga attcccccgg aaccccccggt tggggcccac gcctcgatcg   3420
agcaaaaaaa aaaaaaaaaa aaaaaaaaaa aaaaaaagct tggcgtaatc atggtcatag   3480
```

-continued

```
ctgtttcctg tgtgaaattg ttatccgctc acaattccac acaacatacg agccggaagc   3540
ataaagtgta aagcctgggg tgcctaatga gtgagctaac tcacattaat tgcgttgcgc   3600
tcactgcccg ctttccagtc gggaaacctg tcgtgccagc tgcattaatg aatcggccaa   3660
cgcgcgggga gaggcggttt gcgtattggg cgctcttccg cttcctcgct cactgactcg   3720
ctgcgctcgg tcgttcggct gcggcgagcg gtatcagctc actcaaaggc ggtaatacgg   3780
ttatccacag aatcagggga taacgcagga aagaacatgt gagcaaaagg ccagcaaaag   3840
gccaggaacc gtaaaaaggc cgcgttgctg gcgtttttcc ataggctccg cccccctgac   3900
gagcatcaca aaaatcgacg ctcaagtcag aggtggcgaa acccgacagg actataaaga   3960
taccaggcgt ttccccctgg aagctccctc gtgcgctctc ctgttccgac cctgccgctt   4020
accggatacc tgtccgcctt tctcccttcg ggaagcgtgg cgctttctca tagctcacgc   4080
tgtaggtatc tcagttcggt gtaggtcgtt cgctccaagc tgggctgtgt gcacgaaccc   4140
cccgttcagc ccgaccgctg cgccttatcc ggtaactatc gtcttgagtc caacccggta   4200
agacacgact tatcgccact ggcagcagcc actggtaaca ggattagcag agcgaggtat   4260
gtaggcggtg ctacagagtt cttgaagtgg tggcctaact acggctacac tagaaggaca   4320
gtatttggta tctgcgctct gctgaagcca gttaccttcg gaaaaagagt tggtagctct   4380
tgatccggca aacaaaccac cgctggtagc ggtggttttt ttgtttgcaa gcagcagatt   4440
acgcgcagaa aaaaaggatc tcaagaagat cctttgatct tttctacggg gtctgacgct   4500
cagtggaacg aaaactcacg ttaagggatt ttggtcatga gattatcaaa aaggatcttc   4560
acctagatcc ttttaaatta aaaatgaagt tttaaatcaa tctaaagtat atatgagtaa   4620
acttggtctg acagttacca atgcttaatc agtgaggcac ctatctcagc gatctgtcta   4680
tttcgttcat ccatagttgc ctgactcccc gtcgtgtaga taactacgat acgggagggc   4740
ttaccatctg gccccagtgc tgcaatgata ccgcgagacc cacgctcacc ggctccagat   4800
ttatcagcaa taaaccagcc agccggaagg gccgagcgca gaagtggtcc tgcaacttta   4860
tccgcctcca tccagtctat taattgttgc cgggaagcta gagtaagtag ttcgccagtt   4920
aatagtttgc gcaacgttgt tgccattgct acaggcatcg tggtgtcacg ctcgtcgttt   4980
ggtatggctt cattcagctc cggttcccaa cgatcaaggc gagttacatg atcccccatg   5040
ttgtgcaaaa aagcggttag ctccttcggt cctccgatcg ttgtcagaag taagttggcc   5100
gcagtgttat cactcatggt tatggcagca ctgcataatt ctcttactgt catgccatcc   5160
gtaagatgct tttctgtgac tggtgagtac tcaaccaagt cattctgaga atagtgtatg   5220
cggcgaccga gttgctcttg cccggcgtca atacgggata ataccgcgcc acatagcaga   5280
actttaaaag tgctcatcat tggaaaacgt tcttcggggc gaaaactctc aaggatctta   5340
ccgctgttga gatccagttc gatgtaaccc actcgtgcac ccaactgatc ttcagcatct   5400
tttactttca ccagcgtttc tgggtgagca aaaacaggaa ggcaaaatgc cgcaaaaaag   5460
ggaataaggg cgacacggaa atgttgaata ctcatactct tcctttttca atattattga   5520
agcatttatc agggttattg tctcatgagc ggatacatat ttgaatgtat ttagaaaaat   5580
aaacaaatag gggttccgcg cacatttccc cgaaaagtgc cacctgacgt ctaagaaacc   5640
attattatca tgacattaac ctataaaaat aggcgtatca cgaggccctt tcgtctcgcg   5700
cgtttcggtg atgacggtga aaacctctga cacatgcagc tcccggagac ggtcacagct   5760
tgtctgtaag cggatgccgg gagcagacaa gcccgtcagg gcgcgtcagc gggtgttggc   5820
gggtgtcggg gctggcttaa ctatgcggca tcagagcaga ttgtactgag agtgcaccat   5880
```

-continued atcgacgctc tcccttatgc gactcctgca ttaggaagca gcccagtagt aggttgaggc 5940
cgttgagcac cgccgccgca aggaatggtg catgcaagga gatggcgccc aacagtcccc 6000
cggccacggg gcctgccacc atacccacgc cgaaacaagc gctcatgagc ccgaagtggc 6060
gagcccgatc ttccccatcg gtgatgtcgg cgatataggc gccagcaacc gcacctgtgg 6120
cgccggtgat gccggccacg atgcgtccgg cgtagaggat ctggctagcg atgaccctgc 6180
tgattggttc gctgaccatt tccggggtgc ggaacggcgt taccagaaac tcagaaggtt 6240
cgtccaacca aaccgactct gacggcagtt tacgagagag atgatagggt ctgcttcagt 6300
aagccagatg ctacacaatt aggcttgtac atattgtcgt tagaacgcgg ctacaattaa 6360
tacataacct tatgtatcat acacatacg 6389

<210> SEQ ID NO 3
<211> LENGTH: 4608
<212> TYPE: DNA
<213> ORGANISM: Artificial
<220> FEATURE:
<223> OTHER INFORMATION: Designed DNA(C145A) based on protease originated from human coronavirus

<400> SEQUENCE: 3
atttaggtga cactatagaa ctcacctatc tccccaacac ctaataacat tcaatcactc 60
tttccactaa ccacctatct acatcaccaa gatatcacta gttctcgaga tgagcggctt 120
ccgcaagatg gccttcccca gcggcaaggt cgagggctgc atggtgcagg tcacctgcgg 180
caccactacc ctgaacggcc tgtggctgga tgacaccgtc tactgccccc gccacgtgat 240
ctgcaccgcc gaggacatgc tgaaccccaa ctacgaggac ctgctcatcc gcaagagcaa 300
ccactccttc ctggtgcagg ccggcaacgt ccagctgcgc gtgatcggcc acagcatgca 360
gaactgcctg ctccgcctga aggtggacac cagcaacccc aagaccccca agtacaagtt 420
cgtgcgcatc cagcccggcc agaccttcag cgtgctggcc tgctacaacg gcagccccag 480
cggcgtgtac cagtgcgcca tgcgccccaa ccacaccatc aagggcagct tcctgaacgg 540
gagcgccggc agcgtgggct tcaacatcga ttacgactgc gtaagcttct gctacatgca 600
ccacatggag ctgcccaccg gcgtgcacgc cggcaccgac ctggagggca agttctacgg 660
ccccttcgtg gaccgccaga ccgcccaggc cgccggcacc gacaccacta tcaccctgaa 720
cgtgctggcc tggctgtacg ccgccgtgat caacggcgac cgctggttcc tgaaccgctt 780
caccactacc ctgaacgact tcaacctggt ggccatgaag tacaactacg agcccctgac 840
ccaggaccac gtggacatcc tgggcccct gagcgcccag accggcatcg ccgtcctgga 900
catgtgcgcc gccctgaagg agctgctcca gaacggcatg aacggccgca ccatcctggg 960
cagcaccatc ctggaggacg agttcacccc cttcgacgtc gtgcgccagt gcagcggcgt 1020
gaccttccag taaggatcca tatatagggc ccgggttata attacctcag gtcgacgtcc 1080
catggttttg tatagaattt acggctagcg ccggatgcga cgccggtcgc gtcttatccg 1140
gccttcctat atcaggctgt gtttaagacg ccgccgcttc gcccaaatcc ttatgccggt 1200
tcgacggctg gacaaaatac tgtttatctt cccagcgcag gcaggttaat gtaccacccc 1260
agcagcagcc ggtatccagc gcgtatatac cttccggcgt acctttgccc tccagcgatg 1320
cccagtgacc aaaggcgatg ctgtattctt cagcgacagg gccaggaatc gcaaaccacg 1380
gtttcagtgg ggcaggggcc tcttccggcg attcttacta gctagtatgc ataggtgctg 1440
aaatataaag tttgtgtttc taaaacacac gtggtacgta cgataacgta cagtgttttt 1500

-continued

```
ccctccactt aaatcgaagg gtagtgtctt ggagcgcgcg gagtaaacat atatggttca   1560
tatatgtccg taggcacgta aaaaaagcga gggattcgaa ttcccccgga acccccggtt   1620
ggggcccacg cctcgatcga gcaaaaaaaa aaaaaaaaaa aaaaaaaaaa aaaaaagctt   1680
ggcgtaatca tggtcatagc tgtttcctgt gtgaaattgt tatccgctca caattccaca   1740
caacatacga gccggaagca taaagtgtaa agcctggggt gcctaatgag tgagctaact   1800
cacattaatt gcgttgcgct cactgcccgc tttccagtcg ggaaacctgt cgtgccagct   1860
gcattaatga atcggccaac gcgcggggag aggcggtttg cgtattgggc gctcttccgc   1920
ttcctcgctc actgactcgc tgcgctcggt cgttcggctg cggcgagcgg tatcagctca   1980
ctcaaaggcg gtaatacggt tatccacaga atcaggggat aacgcaggaa agaacatgtg   2040
agcaaaaggc cagcaaaagg ccaggaaccg taaaaaggcc gcgttgctgg cgtttttcca   2100
taggctccgc ccccctgacg agcatcacaa aaatcgacgc tcaagtcaga ggtggcgaaa   2160
cccgacagga ctataaagat accaggcgtt tccccctgga agctccctcg tgcgctctcc   2220
tgttccgacc ctgccgctta ccggatacct gtccgccttt ctcccttcgg gaagcgtggc   2280
gctttctcat agctcacgct gtaggtatct cagttcggtg taggtcgttc gctccaagct   2340
gggctgtgtg cacgaacccc ccgttcagcc cgaccgctgc gccttatccg gtaactatcg   2400
tcttgagtcc aacccggtaa gacacgactt atcgccactg gcagcagcca ctggtaacag   2460
gattagcaga gcgaggtatg taggcggtgc tacagagttc ttgaagtggt ggcctaacta   2520
cggctacact agaaggacag tatttggtat ctgcgctctg ctgaagccag ttaccttcgg   2580
aaaaagagtt ggtagctctt gatccggcaa acaaaccacc gctggtagcg gtggtttttt   2640
tgtttgcaag cagcagatta cgcgcagaaa aaaaggatct caagaagatc ctttgatctt   2700
ttctacgggg tctgacgctc agtggaacga aaactcacgt taagggattt tggtcatgag   2760
attatcaaaa aggatcttca cctagatcct tttaaattaa aaatgaagtt ttaaatcaat   2820
ctaaagtata tatgagtaaa cttggtctga cagttaccaa tgcttaatca gtgaggcacc   2880
tatctcagcg atctgtctat ttcgttcatc catagttgcc tgactccccg tcgtgtagat   2940
aactacgata cgggagggct taccatctgg ccccagtgct gcaatgatac cgcgagaccc   3000
acgctcaccg gctccagatt tatcagcaat aaaccagcca gccggaaggg ccgagcgcag   3060
aagtggtcct gcaactttat ccgcctccat ccagtctatt aattgttgcc gggaagctag   3120
agtaagtagt tcgccagtta atagtttgcg caacgttgtt gccattgcta caggcatcgt   3180
ggtgtcacgc tcgtcgtttg gtatggcttc attcagctcc ggttcccaac gatcaaggcg   3240
agttacatga tcccccatgt tgtgcaaaaa agcggttagc tccttcggtc ctccgatcgt   3300
tgtcagaagt aagttggccg cagtgttatc actcatggtt atggcagcac tgcataattc   3360
tcttactgtc atgccatccg taagatgctt ttctgtgact ggtgagtact caaccaagtc   3420
attctgagaa tagtgtatgc ggcgaccgag ttgctcttgc ccggcgtcaa tacgggataa   3480
taccgcgcca catagcagaa ctttaaaagt gctcatcatt ggaaaacgtt cttcggggcg   3540
aaaactctca aggatcttac cgctgttgag atccagttcg atgtaaccca ctcgtgcacc   3600
caactgatct tcagcatctt ttactttcac cagcgtttct gggtgagcaa aaacaggaag   3660
gcaaaatgcc gcaaaaaagg gaataagggc gacacggaaa tgttgaatac tcatactctt   3720
cctttttcaa tattattgaa gcatttatca gggttattgt ctcatgagcg gatacatatt   3780
tgaatgtatt tagaaaaata aacaaatagg ggttccgcgc acatttcccc gaaaagtgcc   3840
```

-continued

```
acctgacgtc taagaaacca ttattatcat gacattaacc tataaaaata ggcgtatcac   3900

gaggcccttt cgtctcgcgc gtttcggtga tgacggtgaa aacctctgac acatgcagct   3960

cccggagacg gtcacagctt gtctgtaagc ggatgccggg agcagacaag cccgtcaggg   4020

cgcgtcagcg ggtgttggcg ggtgtcgggg ctggcttaac tatgcggcat cagagcagat   4080

tgtactgaga gtgcaccata tcgacgctct cccttatgcg actcctgcat taggaagcag   4140

cccagtagta ggttgaggcc gttgagcacc gccgccgcaa ggaatggtgc atgcaaggag   4200

atggcgccca acagtccccc ggccacgggg cctgccacca tacccacgcc gaaacaagcg   4260

ctcatgagcc cgaagtggcg agcccgatct tccccatcgg tgatgtcggc gatataggcg   4320

ccagcaaccg cacctgtggc gccggtgatg ccggccacga tgcgtccggc gtagaggatc   4380

tggctagcga tgaccctgct gattggttcg ctgaccattt ccggggtgcg gaacggcgtt   4440

accagaaact cagaaggttc gtccaaccaa accgactctg acggcagttt acgagagaga   4500

tgatagggtc tgcttcagta agccagatgc tacacaatta ggcttgtaca tattgtcgtt   4560

agaacgcggc tacaattaat acataacctt atgtatcata cacatacg               4608
```

```
<210> SEQ ID NO 4
<211> LENGTH: 5298
<212> TYPE: DNA
<213> ORGANISM: Artificial
<220> FEATURE:
<223> OTHER INFORMATION: pEU-GST-RS-SARS-3CL

<400> SEQUENCE: 4

atttaggtga cactatagaa ctcacctatc tccccaacac ctaataacat tcaatcactc     60

tttccactaa ccacctatct acatcaccaa gatatcactc gagatggaat cccctatact    120

aggttattgg aaaattaagg gccttgtgca acccactcga cttcttttgg aatatcttga    180

agaaaaatat gaagagcatt tgtatgagcg cgatgaaggt gataaatggc gaaacaaaaa    240

gtttgaattg ggtttggagt ttcccaatct tccttattat attgatggtg atgttaaatt    300

aacacagtct atggccatca tacgttatat agctgacaag cacaacatgt tgggtggttg    360

tccaaaagag cgtgcagaga tttcaatgct tgaaggagcg gttttggata ttagatacgg    420

tgtttcgaga attgcatata gtaaagactt tgaaactctc aaagttgatt ttcttagcaa    480

gctacctgaa atgctgaaaa tgttcgaaga tcgtttatgt cataaaacat atttaaatgg    540

tgatcatgta acccatcctg acttcatgtt gtatgacgct cttgatgttg ttttatacat    600

ggacccaatg tgcctggatg cgttcccaaa attagtttgt tttaaaaaac gtattgaagc    660

tatcccacaa attgataagt acttgaaatc cagcaagtat atagcatggc ctttgcaggg    720

ctggcaagcc acgtttggtg gtggcgacca tcctccaaaa tcggacccac cgcagaccag    780

catcacctct gccgtgctgc agagcggctt ccgcaagatg gccttcccca gcggcaaggt    840

cgagggctgc atggtgcagg tcacctgcgg caccactacc ctgaacggcc tgtggctgga    900

tgacaccgtc tactgccccc gccacgtgat ctgcaccgcc gaggacatgc tgaaccccaa    960

ctacgaggac ctgctcatcc gcaagagcaa ccactccttc ctggtgcagg ccggcaacgt   1020

ccagctgcgc gtgatcggcc acagcatgca gaactgcctg ctccgcctga aggtggacac   1080

cagcaacccc aagaccccca agtacaagtt cgtgcgcatc cagcccggcc agaccttcag   1140

cgtgctggcc tgctacaacg gcagccccag cggcgtgtac cagtgcgcca tgcgccccaa   1200

ccacaccatc aagggcagct tcctgaacgg gagctgcggc agcgtgggct tcaacatcga   1260

ctacgactgc gtaagcttct gctacatgca ccacatggag ctgcccaccg gcgtgcacgc   1320
```

-continued

```
cggcaccgac ctggagggca agttctacgg ccccttcgtg gaccgccaga ccgcccaggc   1380
cgccggcacc gacaccacta tcaccctgaa cgtgctggcc tggctgtacg ccgccgtgat   1440
caacggcgac cgctggttcc tgaaccgctt caccactacc ctgaacgact tcaacctggt   1500
ggccatgaag tacaactacg agcccctgac ccaggaccac gtggacatcc tgggcccccct  1560
gagcgcccag accggcatcg ccgtcctgga catgtgcgcc gccctgaagg agctgctcca   1620
gaacggcatg aacggccgca ccatcctggg cagcaccatc ctggaggacg agttcacccc   1680
cttcgacgtc gtgcgccagt gcagcggcgt gaccttccag taaggatcca tatatagggc   1740
ccgggttata attacctcag gtcgacgtcc catggttttg tatagaattt acggctagcg   1800
ccggatgcga cgccggtcgc gtcttatccg gccttcctat atcaggctgt gtttaagacg   1860
ccgccgcttc gcccaaatcc ttatgccggt tcgacggctg gacaaaatac tgtttatctt   1920
cccagcgcag gcaggttaat gtaccacccc agcagcagcc ggtatccagc gcgtatatac   1980
cttccggcgt acctttgccc tccagcgatg cccagtgacc aaaggcgatg ctgtattctt   2040
cagcgacagg gccaggaatc gcaaaccacg gtttcagtgg ggcaggggcc tcttccggcg   2100
attcttacta gctagtatgc ataggtgctg aaatataaag tttgtgtttc taaaacacac   2160
gtggtacgta cgataacgta cagtgttttt ccctccactt aaatcgaagg gtagtgtctt   2220
ggagcgcgcg gagtaaacat atatggttca tatatgtccg taggcacgta aaaaaagcga   2280
gggattcgaa ttcccccgga acccccggtt ggggcccacg cctcgatcga gcaaaaaaaa   2340
aaaaaaaaaa aaaaaaaaaa aaaaaagctt ggcgtaatca tggtcatagc tgtttcctgt   2400
gtgaaattgt tatccgctca caattccaca caacatacga gccggaagca taaagtgtaa   2460
agcctggggt gcctaatgag tgagctaact cacattaatt gcgttgcgct cactgcccgc   2520
tttccagtcg ggaaacctgt cgtgccagct gcattaatga atcggccaac gcgcggggag   2580
aggcggtttg cgtattgggc gctcttccgc ttcctcgctc actgactcgc tgcgctcggt   2640
cgttcggctg cggcgagcgg tatcagctca ctcaaaggcg gtaatacggt tatccacaga   2700
atcaggggat aacgcaggaa agaacatgtg agcaaaaggc cagcaaaagg ccaggaaccg   2760
taaaaaggcc gcgttgctgg cgtttttcca taggctccgc ccccctgacg agcatcacaa   2820
aaatcgacgc tcaagtcaga ggtggcgaaa cccgacagga ctataaagat accaggcgtt   2880
tccccctgga agctccctcg tgcgctctcc tgttccgacc ctgccgctta ccggatacct   2940
gtccgccttt ctcccttcgg gaagcgtggc gctttctcat agctcacgct gtaggtatct   3000
cagttcggtg taggtcgttc gctccaagct gggctgtgtg cacgaacccc ccgttcagcc   3060
cgaccgctgc gccttatccg gtaactatcg tcttgagtcc aacccggtaa gacacgactt   3120
atcgccactg gcagcagcca ctggtaacag gattagcaga gcgaggtatg taggcggtgc   3180
tacagagttc ttgaagtggt ggcctaacta cggctacact agaaggacag tatttggtat   3240
ctgcgctctg ctgaagccag ttaccttcgg aaaaagagtt ggtagctctt gatccggcaa   3300
acaaaccacc gctggtagcg gtggtttttt tgtttgcaag cagcagatta cgcgcagaaa   3360
aaaaggatct caagaagatc ctttgatctt ttctacgggg tctgacgctc agtggaacga   3420
aaactcacgt taagggattt tggtcatgag attatcaaaa aggatcttca cctagatcct   3480
tttaaattaa aaatgaagtt ttaaatcaat ctaaagtata tatgagtaaa cttggtctga   3540
cagttaccaa tgcttaatca gtgaggcacc tatctcagcg atctgtctat ttcgttcatc   3600
catagttgcc tgactccccg tcgtgtagat aactacgata cgggagggct taccatctgg   3660
```

-continued ccccagtgct gcaatgatac cgcgagaccc acgctcaccg gctccagatt tatcagcaat 3720
aaaccagcca gccggaaggg ccgagcgcag aagtggtcct gcaactttat ccgcctccat 3780
ccagtctatt aattgttgcc gggaagctag agtaagtagt tcgccagtta atagtttgcg 3840
caacgttgtt gccattgcta caggcatcgt ggtgtcacgc tcgtcgtttg gtatggcttc 3900
attcagctcc ggttcccaac gatcaaggcg agttacatga tcccccatgt tgtgcaaaaa 3960
agcggttagc tccttcggtc ctccgatcgt tgtcagaagt aagttggccg cagtgttatc 4020
actcatggtt atggcagcac tgcataattc tcttactgtc atgccatccg taagatgctt 4080
ttctgtgact ggtgagtact caaccaagtc attctgagaa tagtgtatgc ggcgaccgag 4140
ttgctcttgc ccggcgtcaa tacgggataa taccgcgcca catagcagaa ctttaaaagt 4200
gctcatcatt ggaaaacgtt cttcggggcg aaaactctca aggatcttac cgctgttgag 4260
atccagttcg atgtaaccca ctcgtgcacc caactgatct tcagcatctt ttactttcac 4320
cagcgtttct gggtgagcaa aaacaggaag gcaaaatgcc gcaaaaaagg gaataagggc 4380
gacacggaaa tgttgaatac tcatactctt cctttttcaa tattattgaa gcatttatca 4440
gggttattgt ctcatgagcg gatacatatt tgaatgtatt tagaaaaata aacaaatagg 4500
ggttccgcgc acatttcccc gaaaagtgcc acctgacgtc taagaaacca ttattatcat 4560
gacattaacc tataaaaata ggcgtatcac gaggcccttt cgtctcgcgc gtttcggtga 4620
tgacggtgaa aacctctgac acatgcagct cccggagacg gtcacagctt gtctgtaagc 4680
ggatgccggg agcagacaag cccgtcaggg cgcgtcagcg ggtgttggcg ggtgtcgggg 4740
ctggcttaac tatgcggcat cagagcagat tgtactgaga gtgcaccata tcgacgctct 4800
cccttatgcg actcctgcat taggaagcag cccagtagta ggttgaggcc gttgagcacc 4860
gccgccgcaa ggaatggtgc atgcaaggag atggcgccca acagtccccc ggccacgggg 4920
cctgccacca tacccacgcc gaaacaagcg ctcatgagcc cgaagtggcg agcccgatct 4980
tccccatcgg tgatgtcggc gatataggcg ccagcaaccg cacctgtggc gccggtgatg 5040
ccggccacga tgcgtccggc gtagaggatc tggctagcga tgaccctgct gattggttcg 5100
ctgaccattt ccggggtgcg gaacggcgtt accagaaact cagaaggttc gtccaaccaa 5160
accgactctg acggcagttt acgagagaga tgatagggtc tgcttcagta agccagatgc 5220
tacacaatta ggcttgtaca tattgtcgtt agaacgcggc tacaattaat acataacctt 5280
atgtatcata cacatacg 5298

<210> SEQ ID NO 5
<211> LENGTH: 5353
<212> TYPE: DNA
<213> ORGANISM: Artificial
<220> FEATURE:
<223> OTHER INFORMATION: pEU-GFP-RS-SARS-3CL

<400> SEQUENCE: 5
atttaggtga cactatagaa ctcacctatc tccccaacac ctaataacat tcaatcactc 60
tttccactaa ccacctatct acatcaccaa gatatcactc gagcatggtg agcaagggcg 120
aggagctgtt caccggggtg gtgcccatcc tggtcgagct ggacggcgac gtgaacggcc 180
acaagttcag cgtgtccggc gagggcgagg gcgatgccac ctacggcaag ctgaccctga 240
agttcatctg caccaccggc aagctgcccg tgccctggcc caccctcgtg accaccttca 300
cctacggcgt gcagtgcttc agccgctacc ccgaccacat gaagcagcac gacttcttca 360
agtccgccat gcccgaaggc tacgtccagg agcgcaccat cttcttcaag gacgacggca 420

-continued

```
actacaagac ccgcgccgag gtgaagttcg agggcgacac cctggtgaac cgcatcgagc    480
tgaagggcat cgacttcaag gaggacggca acatcctggg gcacaagctg gagtacaact    540
acaacagcca caacgtctat atcatggccg acaagcagaa gaacggcatc aaggtgaact    600
tcaagatccg ccacaacatc gaggacggca gcgtgcagct cgccgaccac taccagcaga    660
acacccccat cggcgacggc cccgtgctgc tgcccgacaa ccactacctg agcacccagt    720
ccgccctgag caaagacccc aacgagaagc gcgatcacat ggtcctgctg gagttcgtga    780
ccgccgccgg gatcactcac ggcatggacg agctgtacaa gcccccccag accagcatca    840
cctctgccgt gctgcagagc ggcttccgca agatggcctt ccccagcggc aaggtcgagg    900
gctgcatggt gcaggtcacc tgcggcacca ctaccctgaa cggcctgtgg ctggatgaca    960
ccgtctactg cccccgccac gtgatctgca ccgccgagga catgctgaac cccaactacg   1020
aggacctgct catccgcaag agcaaccact ccttcctggt gcaggccggc aacgtccagc   1080
tgcgcgtgat cggccacagc atgcagaact gcctgctccg cctgaaggtg gacaccagca   1140
accccaagac ccccaagtac aagttcgtgc gcatccagcc cggccagacc ttcagcgtgc   1200
tggcctgcta caacggcagc cccagcggcg tgtaccagtg cgccatgcgc cccaaccaca   1260
ccatcaaggg cagcttcctg aacgggagct gcggcagcgt gggcttcaac atcgactacg   1320
actgcgtaag cttctgctac atgcaccaca tggagctgcc caccggcgtg cacgccggca   1380
ccgacctgga gggcaagttc tacggcccct tcgtggaccg ccagaccgcc caggccgccg   1440
gcaccgacac caccatcacc ctgaacgtgc tggcctggct gtacgccgcc gtgatcaacg   1500
gcgaccgctg gttcctgaac cgcttcacca ctaccctgaa cgacttcaac ctggtggcca   1560
tgaagtacaa ctacgagccc ctgacccagg accacgtgga catcctgggc cccctgagcg   1620
cccagaccgg catcgccgtc ctggacatgt gcgccgccct gaaggagctg ctccagaacg   1680
gcatgaacgg ccgcaccatc ctgggcagca ccatcctgga ggacgagttc accccctcg    1740
acgtcgtgcg ccagtgcagc ggcgtgacct tccagtaagg atccatatat agggcccggg   1800
ttataattac ctcaggtcga cgtcccatgg ttttgtatag aatttacggc tagcgccgga   1860
tgcgacgccg gtcgcgtctt atccggcctt cctatatcag gctgtgttta agacgccgcc   1920
gcttcgccca aatccttatg ccggttcgac ggctggacaa aatactgttt atcttcccag   1980
cgcaggcagg ttaatgtacc accccagcag cagccggtat ccagcgcgta tataccttcc   2040
ggcgtacctt tgccctccag cgatgcccag tgaccaaagg cgatgctgta ttcttcagcg   2100
acagggccag gaatcgcaaa ccacggtttc agtggggcag ggcctcttc cggcgattct    2160
tactagctag tatgcatagg tgctgaaata taaagtttgt gtttctaaaa cacacgtggt   2220
acgtacgata acgtacagtg tttttccctc cacttaaatc gaagggtagt gtcttggagc   2280
gcgcggagta aacatatatg gttcatatat gtccgtaggc acgtaaaaaa agcgagggat   2340
tcgaattccc ccggaacccc cggttggggc ccacgcctcg atcgagcaaa aaaaaaaaaa   2400
aaaaaaaaaa aaaaaaaaaa agcttggcgt aatcatggtc atagctgttt cctgtgtgaa   2460
attgttatcc gctcacaatt ccacacaaca tacgagccgg aagcataaag tgtaaagcct   2520
ggggtgccta atgagtgagc taactcacat taattgcgtt gcgctcactg cccgctttcc   2580
agtcgggaaa cctgtcgtgc cagctgcatt aatgaatcgg ccaacgcgcg gggagaggcg   2640
gtttgcgtat tgggcgctct tccgcttcct cgctcactga ctcgctgcgc tcggtcgttc   2700
ggctgcggcg agcggtatca gctcactcaa aggcggtaat acggttatcc acagaatcag   2760
```

-continued

```
gggataacgc aggaaagaac atgtgagcaa aaggccagca aaaggccagg aaccgtaaaa   2820
aggccgcgtt gctggcgttt ttccataggc tccgcccccc tgacgagcat cacaaaaatc   2880
gacgctcaag tcagaggtgg cgaaacccga caggactata aagataccag gcgtttcccc   2940
ctggaagctc cctcgtgcgc tctcctgttc cgaccctgcc gcttaccgga tacctgtccg   3000
cctttctccc ttcgggaagc gtggcgcttt ctcatagctc acgctgtagg tatctcagtt   3060
cggtgtaggt cgttcgctcc aagctgggct gtgtgcacga accccccgtt cagcccgacc   3120
gctgcgcctt atccggtaac tatcgtcttg agtccaaccc ggtaagacac gacttatcgc   3180
cactggcagc agccactggt aacaggatta gcagagcgag gtatgtaggc ggtgctacag   3240
agttcttgaa gtggtggcct aactacggct acactagaag gacagtattt ggtatctgcg   3300
ctctgctgaa gccagttacc ttcggaaaaa gagttggtag ctcttgatcc ggcaaacaaa   3360
ccaccgctgg tagcggtggt ttttttgttt gcaagcagca gattacgcgc agaaaaaaag   3420
gatctcaaga agatcctttg atcttttcta cggggtctga cgctcagtgg aacgaaaact   3480
cacgttaagg gattttggtc atgagattat caaaaaggat cttcacctag atccttttaa   3540
attaaaaatg aagttttaaa tcaatctaaa gtatatatga gtaaacttgg tctgacagtt   3600
accaatgctt aatcagtgag gcacctatct cagcgatctg tctatttcgt tcatccatag   3660
ttgcctgact ccccgtcgtg tagataacta cgatacggga gggcttacca tctggcccca   3720
gtgctgcaat gataccgcga gacccacgct caccggctcc agatttatca gcaataaacc   3780
agccagccgg aagggccgag cgcagaagtg gtcctgcaac tttatccgcc tccatccagt   3840
ctattaattg ttgccgggaa gctagagtaa gtagttcgcc agttaatagt ttgcgcaacg   3900
ttgttgccat tgctacaggc atcgtggtgt cacgctcgtc gtttggtatg gcttcattca   3960
gctccggttc ccaacgatca aggcgagtta catgatcccc catgttgtgc aaaaaagcgg   4020
ttagctcctt cggtcctccg atcgttgtca gaagtaagtt ggccgcagtg ttatcactca   4080
tggttatggc agcactgcat aattctctta ctgtcatgcc atccgtaaga tgcttttctg   4140
tgactggtga gtactcaacc aagtcattct gagaatagtg tatgcggcga ccgagttgct   4200
cttgcccggc gtcaatacgg gataataccg cgccacatag cagaacttta aaagtgctca   4260
tcattggaaa acgttcttcg gggcgaaaac tctcaaggat cttaccgctg ttgagatcca   4320
gttcgatgta acccactcgt gcacccaact gatcttcagc atcttttact ttcaccagcg   4380
tttctgggtg agcaaaaaca ggaaggcaaa atgccgcaaa aaagggaata agggcgacac   4440
ggaaatgttg aatactcata ctcttccttt ttcaatatta ttgaagcatt tatcagggtt   4500
attgtctcat gagcggatac atatttgaat gtatttagaa aaataaacaa ataggggttc   4560
cgcgcacatt tccccgaaaa gtgccacctg acgtctaaga aaccattatt atcatgacat   4620
taacctataa aaataggcgt atcacgaggc cctttcgtct cgcgcgtttc ggtgatgacg   4680
gtgaaaacct ctgacacatg cagctcccgg agacggtcac agcttgtctg taagcggatg   4740
ccgggagcag acaagcccgt cagggcgcgt cagcgggtgt tggcgggtgt cggggctggc   4800
ttaactatgc ggcatcagag cagattgtac tgagagtgca ccatatcgac gctctccctt   4860
atgcgactcc tgcattagga agcagcccag tagtaggttg aggccgttga gcaccgccgc   4920
cgcaaggaat ggtgcatgca aggagatggc gcccaacagt cccccggcca cggggcctgc   4980
caccataccc acgccgaaac aagcgctcat gagcccgaag tggcgagccc gatcttcccc   5040
atcggtgatg tcggcgatat aggcgccagc aaccgcacct gtggcgccgg tgatgccggc   5100
cacgatgcgt ccggcgtaga ggatctggct agcgatgacc ctgctgattg gttcgctgac   5160
```

-continued

```
catttccggg gtgcggaacg gcgttaccag aaactcagaa ggttcgtcca accaaaccga   5220

ctctgacggc agtttacgag agagatgata gggtctgctt cagtaagcca gatgctacac   5280

aattaggctt gtacatattg tcgttagaac gcggctacaa ttaatacata accttatgta   5340

tcatacacat acg                                                      5353


<210> SEQ ID NO 6
<211> LENGTH: 115
<212> TYPE: DNA
<213> ORGANISM: Artificial
<220> FEATURE:
<223> OTHER INFORMATION: Primer for cloning SARS protease gene

<400> SEQUENCE: 6

cggcatgaac ggccgcacca tcctgggcag caccatcctg gaggacgagt tcaccccctt     60

cgacgtcgtg cgccagtgca gcggcgtgac cttccagtaa ggatccacta gttct         115


<210> SEQ ID NO 7
<211> LENGTH: 35
<212> TYPE: DNA
<213> ORGANISM: Artificial
<220> FEATURE:
<223> OTHER INFORMATION: Primer for cloning SARS protease gene

<400> SEQUENCE: 7

ctgaaggagc tgctccagaa cggcatgaac ggccg                                35


<210> SEQ ID NO 8
<211> LENGTH: 115
<212> TYPE: DNA
<213> ORGANISM: Artificial
<220> FEATURE:
<223> OTHER INFORMATION: Primer for cloning SARS protease gene

<400> SEQUENCE: 8

catgaagtac aactacgagc ccctgaccca ggaccacgtg gacatcctgg gcccccctgag     60

cgcccagacc ggcatcgccg tcctggacat gtgcgccgcc ctgaaggagc tgctc         115


<210> SEQ ID NO 9
<211> LENGTH: 35
<212> TYPE: DNA
<213> ORGANISM: Artificial
<220> FEATURE:
<223> OTHER INFORMATION: Primer for cloning SARS protease gene

<400> SEQUENCE: 9

aacgacttca acctggtggc catgaagtac aacta                                35


<210> SEQ ID NO 10
<211> LENGTH: 115
<212> TYPE: DNA
<213> ORGANISM: Artificial
<220> FEATURE:
<223> OTHER INFORMATION: Primer for cloning SARS protease gene

<400> SEQUENCE: 10

cggcaccgac accaccatca ccctgaacgt gctggcctgg ctgtacgccg ccgtgatcaa     60

cggcgaccgc tggttcctga accgcttcac cactaccctg aacgacttca acctg         115


<210> SEQ ID NO 11
<211> LENGTH: 35
<212> TYPE: DNA
```

-continued

<213> ORGANISM: Artificial
<220> FEATURE:
<223> OTHER INFORMATION: Primer for cloning SARS protease gene

<400> SEQUENCE: 11
cgccagaccg cccaggccgc cggcaccgac accac 35

<210> SEQ ID NO 12
<211> LENGTH: 99
<212> TYPE: DNA
<213> ORGANISM: Artificial
<220> FEATURE:
<223> OTHER INFORMATION: Primer for cloning SARS protease gene

<400> SEQUENCE: 12
tgctacatgc accacatgga gctgcccacc ggcgtgcacg ccggcaccga cctggagggc 60
aagttctacg gccccttcgt ggaccgccag accgcccag 99

<210> SEQ ID NO 13
<211> LENGTH: 35
<212> TYPE: DNA
<213> ORGANISM: Artificial
<220> FEATURE:
<223> OTHER INFORMATION: Primer for cloning SARS protease gene

<400> SEQUENCE: 13
actacgactg cgtaagcttc tgctacatgc accac 35

<210> SEQ ID NO 14
<211> LENGTH: 115
<212> TYPE: DNA
<213> ORGANISM: Artificial
<220> FEATURE:
<223> OTHER INFORMATION: Primer for cloning SARS protease gene

<400> SEQUENCE: 14
ccagccacag gccgttcagg gtagtggtgc cgcaggtgac ctgcaccatg cagccctcga 60
ccttgccgct ggggaaggcc atcttgcgga agccgctcat ctcgaggggg ggccc 115

<210> SEQ ID NO 15
<211> LENGTH: 35
<212> TYPE: DNA
<213> ORGANISM: Artificial
<220> FEATURE:
<223> OTHER INFORMATION: Primer for cloning SARS protease gene

<400> SEQUENCE: 15
ggggcagtag acggtgtcat ccagccacag gccgt 35

<210> SEQ ID NO 16
<211> LENGTH: 115
<212> TYPE: DNA
<213> ORGANISM: Artificial
<220> FEATURE:
<223> OTHER INFORMATION: Primer for cloning SARS protease gene

<400> SEQUENCE: 16
cgttgccggc ctgcaccagg aaggagtggt tgctcttgcg gatgagcagg tcctcgtagt 60
tggggttcag catgtcctcg gcggtgcaga tcacgtggcg ggggcagtag acggt 115

<210> SEQ ID NO 17
<211> LENGTH: 35
<212> TYPE: DNA
<213> ORGANISM: Artificial

-continued

<220> FEATURE:
<223> OTHER INFORMATION: Primer for cloning SARS protease gene

<400> SEQUENCE: 17
gccgatcacg cgcagctgga cgttgccggc ctgca 35

<210> SEQ ID NO 18
<211> LENGTH: 115
<212> TYPE: DNA
<213> ORGANISM: Artificial
<220> FEATURE:
<223> OTHER INFORMATION: Primer for cloning SARS protease gene

<400> SEQUENCE: 18
tgaaggtctg gccgggctgg atgcgcacga acttgtactt gggggtcttg ggttgctgg 60 tgtccacctt caggcggagc aggcagttct gcatgctgtg gccgatcacg cgcag 115

<210> SEQ ID NO 19
<211> LENGTH: 35
<212> TYPE: DNA
<213> ORGANISM: Artificial
<220> FEATURE:
<223> OTHER INFORMATION: Primer for cloning SARS protease gene

<400> SEQUENCE: 19
gttgtagcag gccagcacgc tgaaggtctg gccgg 35

<210> SEQ ID NO 20
<211> LENGTH: 115
<212> TYPE: DNA
<213> ORGANISM: Artificial
<220> FEATURE:
<223> OTHER INFORMATION: Primer for cloning SARS protease gene

<400> SEQUENCE: 20
cgatgttgaa gcccacgctg ccgcagctcc cgttcaggaa gctgcccttg atggtgtggt 60
tggggcgcat ggcgcactgg tacacgccgc tggggctgcc gttgtagcag gccag 115

<210> SEQ ID NO 21
<211> LENGTH: 37
<212> TYPE: DNA
<213> ORGANISM: Artificial
<220> FEATURE:
<223> OTHER INFORMATION: Primer for cloning SARS protease gene

<400> SEQUENCE: 21
gagaagctta cgcagtcgta gtcgatgttg aagccca 37

<210> SEQ ID NO 22
<211> LENGTH: 21
<212> TYPE: DNA
<213> ORGANISM: Artificial
<220> FEATURE:
<223> OTHER INFORMATION: Spu primer

<400> SEQUENCE: 22
gcgtagcatt taggtgacac t 21

<210> SEQ ID NO 23
<211> LENGTH: 20
<212> TYPE: DNA
<213> ORGANISM: Artificial
<220> FEATURE:
<223> OTHER INFORMATION: AODA2303 primer -continued

<400> SEQUENCE: 23
gtcagacccc gtagaaaaga 20

<210> SEQ ID NO 24
<211> LENGTH: 29
<212> TYPE: DNA
<213> ORGANISM: Artificial
<220> FEATURE:
<223> OTHER INFORMATION: GFP-RS-GUS (E01-XhoI-A1)

<400> SEQUENCE: 24
gagactcgag tgatatcttg gtgatgtag 29

<210> SEQ ID NO 25
<211> LENGTH: 69
<212> TYPE: DNA
<213> ORGANISM: Artificial
<220> FEATURE:
<223> OTHER INFORMATION: GFP-RS-GUS (GUS-RS-S1)

<400> SEQUENCE: 25
gagactgcag agcggcttcc gcaagatggc cttccccagc ggcaaggtga tgttacgtcc 60
tgtagaaac 69

<210> SEQ ID NO 26
<211> LENGTH: 30
<212> TYPE: DNA
<213> ORGANISM: Artificial
<220> FEATURE:
<223> OTHER INFORMATION: GFP-RS-GUS (GFP-XhoI-S1)

<400> SEQUENCE: 26
gagactcgag aatggtgagc aagggcgagg 30

<210> SEQ ID NO 27
<211> LENGTH: 59
<212> TYPE: DNA
<213> ORGANISM: Artificial
<220> FEATURE:
<223> OTHER INFORMATION: GFP-RS-GUS (GFP-RS-A1)

<400> SEQUENCE: 27
gagactgcag cacggcagag gtgatgctgg tctggggggg cttgtacagc tcgtccatg 59

<210> SEQ ID NO 28
<211> LENGTH: 30
<212> TYPE: DNA
<213> ORGANISM: Artificial
<220> FEATURE:
<223> OTHER INFORMATION: GFP-RS-SA3CL pro (RS-3CL-S1)

<400> SEQUENCE: 28
gagactgcag agcggcttcc gcaagatggc 30

<210> SEQ ID NO 29
<211> LENGTH: 17
<212> TYPE: DNA
<213> ORGANISM: Artificial
<220> FEATURE:
<223> OTHER INFORMATION: GFP-RS-SA3CL pro (M13)

<400> SEQUENCE: 29
gtaaaacgac ggccagt 17

-continued

<210> SEQ ID NO 30
<211> LENGTH: 23
<212> TYPE: DNA
<213> ORGANISM: Artificial
<220> FEATURE:
<223> OTHER INFORMATION: GST-RS-SA3CL pro (GST-RS-sen)

<400> SEQUENCE: 30
gagactcgag atggaatccc cta 23

<210> SEQ ID NO 31
<211> LENGTH: 59
<212> TYPE: DNA
<213> ORGANISM: Artificial
<220> FEATURE:
<223> OTHER INFORMATION: GST-RS-SA3CL pro (GST-RS-anti)

<400> SEQUENCE: 31
gagactgcag cacggcagag gtgatgctgg tctgcggtgg gtccgatttt ggaggatgg 59

<210> SEQ ID NO 32
<211> LENGTH: 306
<212> TYPE: PRT
<213> ORGANISM: SA3CL pro

<400> SEQUENCE: 32

Ser Gly Phe Arg Lys Met Ala Phe Pro Ser Gly Lys Val Glu Gly Cys
1 5 10 15

Met Val Gln Val Thr Cys Gly Thr Thr Thr Leu Asn Gly Leu Trp Leu
20 25 30

Asp Asp Thr Val Tyr Cys Pro Arg His Val Ile Cys Thr Ala Glu Asp
35 40 45

Met Leu Asn Pro Asn Tyr Glu Asp Leu Leu Ile Arg Lys Ser Asn His
50 55 60

Ser Phe Leu Val Gln Ala Gly Asn Val Gln Leu Arg Val Ile Gly His
65 70 75 80

Ser Met Gln Asn Cys Leu Leu Arg Leu Lys Val Asp Thr Ser Asn Pro
85 90 95

Lys Thr Pro Lys Tyr Lys Phe Val Arg Ile Gln Pro Gly Gln Thr Phe
100 105 110

Ser Val Leu Ala Cys Tyr Asn Gly Ser Pro Ser Gly Val Tyr Gln Cys
115 120 125

Ala Met Arg Pro Asn His Thr Ile Lys Gly Ser Phe Leu Asn Gly Ser
130 135 140

Cys Gly Ser Val Gly Phe Asn Ile Asp Tyr Asp Cys Val Ser Phe Cys
145 150 155 160

Tyr Met His His Met Glu Leu Pro Thr Gly Val His Ala Gly Thr Asp
165 170 175

Leu Glu Gly Lys Phe Tyr Gly Pro Phe Val Asp Arg Gln Thr Ala Gln
180 185 190

Ala Ala Gly Thr Asp Thr Thr Ile Thr Leu Asn Val Leu Ala Trp Leu
195 200 205

Tyr Ala Ala Val Ile Asn Gly Asp Arg Trp Phe Leu Asn Arg Phe Thr
210 215 220

Thr Thr Leu Asn Asp Phe Asn Leu Val Ala Met Lys Tyr Asn Tyr Glu
225 230 235 240

Pro Leu Thr Gln Asp His Val Asp Ile Leu Gly Pro Leu Ser Ala Gln
245 250 255

-continued

```
Thr Gly Ile Ala Val Leu Asp Met Cys Ala Ala Leu Lys Glu Leu Leu
            260                 265                 270

Gln Asn Gly Met Asn Gly Arg Thr Ile Leu Gly Ser Thr Ile Leu Glu
        275                 280                 285

Asp Glu Phe Thr Pro Phe Asp Val Val Arg Gln Cys Ser Gly Val Thr
    290                 295                 300

Phe Gln
305
```

The invention claimed is:

1. A method for searching a drug to a protease derived from SARS using a cell-free protein synthesis means with the use of a wheat embryo extract solution comprising at least steps 3) to 5) of the following steps:

1) synthesizing a gene comprising a gene encoding the protease derived from SARS, wherein the step is based on base sequence information of the gene of the protease derived from SARS, 2) synthesizing an mRNA from the gene synthesized in step 1), 3) synthesizing the protease derived from SARS using a cell-free protein synthesis system with the use of a wheat embryo extract solution, using the mRNA synthesized in step 2) as a translation template or the gene synthesized in step 1) as a transcription template, 4) determining the reactivity of a candidate drug to the protease derived from SARS by adding the candidate drug to the cell-free protein synthesis system with the use of a wheat embryo extract solution, and 5) screening a drug to the protease derived from SARS by using the reactivity as an indicator, and wherein the wheat embryo extract solution is a cell-free protein synthesis means with a wheat embryo extract from which an endosperm and a low molecular synthesis inhibitor are substantially removed.

2. The method for searching a drug according to the claim 1, wherein the indicator of reactivity to the protease derived from SARS is based on the reactivity to autodigestion of the protease derived from SARS.

3. The method for searching a drug according to the claim 1, wherein the indicator of reactivity to the protease derived from SARS is based on the reactivity to substrate recognition of the protease derived from SARS.

4. The method for searching a drug according to the claim 1, wherein the indicator of reactivity to the protease derived from SARS is based on the protease derived from SARS' autodigestion in a folding process, inhibition or termination of folding, or induction of misfolding.

5. The method for searching a drug according to claim 1, wherein the steps 3) to 5) or 2) to 5) are conducted in a single reaction system.

* * * * *